US012758355B2

(12) United States Patent
Yang et al.

(10) Patent No.: US 12,758,355 B2
(45) Date of Patent: Oct. 13, 2026

(54) SURGERY DEVICE AND OPERATING METHOD USING THE SAME

(71) Applicant: ROEN Surgical, Inc., Daejeon (KR)

(72) Inventors: Un-Je Yang, Gyeonggi-do (KR); Duk-Sang Kim, Seoul (KR); Duk-Yoo Kong, Seoul (KR); Dong-Ho Lee, Daejeon (KR); Tuani De Sa Rosa, Seoul (KR); Hyunwoo Baek, Seoul (KR)

(73) Assignee: ROEN Surgical, Inc., Daejeon (KR)

(*) Notice: Subject to any disclaimer, the term of this patent is extended or adjusted under 35 U.S.C. 154(b) by 345 days.

(21) Appl. No.: 18/384,727

(22) Filed: Oct. 27, 2023

(65) Prior Publication Data

US 2025/0090267 A1 Mar. 20, 2025

(30) Foreign Application Priority Data

Sep. 19, 2023 (KR) ........................ 10-2023-0124495
Sep. 19, 2023 (KR) ........................ 10-2023-0124516
Sep. 19, 2023 (KR) ........................ 10-2023-0124527

(51) Int. Cl.
*A61B 90/50* (2016.01)
*A61B 17/00* (2006.01)

(52) U.S. Cl.
CPC .............. *A61B 90/50* (2016.02); *A61B 17/00* (2013.01); *A61B 2017/00398* (2013.01); *A61B 2090/506* (2016.02)

(58) Field of Classification Search
CPC .................... A61B 90/50; A61B 17/00; A61B 2017/00398; A61B 2090/506;
(Continued)

(56) References Cited

U.S. PATENT DOCUMENTS 5,397,323 A 3/1995 Taylor et al.
6,702,805 B1 * 3/2004 Stuart .................... A61B 34/71
(Continued)

FOREIGN PATENT DOCUMENTS

CN 212346718 U * 1/2021
CN 115317094 A * 11/2022 ............. A61B 34/10
(Continued)

OTHER PUBLICATIONS

Machine Translation of CN115317094A (Year: 2022).*
(Continued)

*Primary Examiner* — Ellis B. Ramirez

(74) *Attorney, Agent, or Firm* — Morgan, Lewis & Bockius LLP

(57) ABSTRACT

Provided is a surgical device capable of performing a stable and precise operation and an operation method using the same.

The surgical device according to an embodiment of the present invention includes a surgical instrument module, a dual parallelogram module connected to a rear side of the surgical instrument module and including a plurality of power transmission units, so that each power transmission unit performs motion driving with two degrees of freedom of pitch and roll driving, and a linear drive module that is linearly driven in one direction to transmit a linear driving force to the dual parallel program module.

16 Claims, 17 Drawing Sheets

(58) Field of Classification Search

CPC ........ A61B 2034/301; A61B 2034/302; A61B 2034/303; A61B 2034/304; A61B 34/30

USPC ....... 700/245; 606/130; 74/490.03; 600/106; 901/16, 23, 30, 41

See application file for complete search history.

(56) References Cited

U.S. PATENT DOCUMENTS

| | | | | |
|---|---|---|---|---|
| 7,021,173 | B2 * | 4/2006 | Stoianovici | B25J 18/007 |
| 10,322,514 | B2 * | 6/2019 | Vander Poorten | B25J 18/007 |
| 11,426,198 | B2 * | 8/2022 | Fenster | A61B 6/502 |
| 2005/0043718 | A1 | 2/2005 | Madhani et al. | |
| 2009/0234369 | A1 * | 9/2009 | Bax | A61B 34/30 |
| 2011/0230894 | A1 * | 9/2011 | Simaan | A61B 1/05 |
| 2012/0211006 | A1 * | 8/2012 | Gill | A61B 34/30 |
| 2014/0039314 | A1 * | 2/2014 | Stoianovici | A61B 8/0841 |
| 2015/0297934 | A1 * | 10/2015 | Agrawal | A61H 1/0266 |
| 2020/0405417 | A1 * | 12/2020 | Shelton, IV | A61B 90/361 |
| 2021/0137618 | A1 * | 5/2021 | Simi | A61B 34/37 |
| 2022/0338954 | A1 | 10/2022 | Chablat et al. | |
| 2023/0415332 | A1 * | 12/2023 | Kwon | A61B 34/30 |
| 2024/0058583 | A1 * | 2/2024 | Boulangé | A61M 25/0113 |

FOREIGN PATENT DOCUMENTS

| | | | | |
|---|---|---|---|---|
| EP | 2429441 | B1 * | 4/2013 | A61B 34/70 |
| KR | 10-2009-0119366 | A | 11/2009 | |
| KR | 10-2017-0125174 | A | 11/2017 | |
| KR | 10-2022-0065279 | A | 5/2022 | |
| KR | 10-2502444 | B1 | 2/2023 | |
| WO | 2022/103166 | A1 | 5/2022 | |

OTHER PUBLICATIONS

Extended European Search Report issued in corresponding European Patent Application No. 23206566.4, dated Jul. 17, 2024.

Office Action issued in corresponding Korean Patent Application No. 10-2023-0124495, dated Jan. 14, 2026.

Office Action issued in corresponding Korean Patent Application No. 10-2023-0124516, dated Jan. 14, 2026.

Office Action issued in corresponding Korean Patent Application No. 10-2023-0124527, dated Jan. 14, 2026.

Partial European Search Report issued in corresponding European Patent Application No. 23206566.4, dated Apr. 26, 2024.

* cited by examiner (a) (b)

SURGERY DEVICE AND OPERATING METHOD USING THE SAME

CROSS-REFERENCE TO RELATED APPLICATIONS

This U.S. non-provisional patent application claims priority under 35 U.S.C. § 119 of Korean Patent Application No. 10-2023-0124495, 10-2023-0124516 and 10-2023-0124527, filed on Nov. 19, 2023, the entire contents of which are hereby incorporated by reference.

BACKGROUND

The present invention relates to a surgical device and an operation method using the same, and more particularly, to a surgical device capable of performing a stable and precise operation and an operation method using the same.

In general, a parallelogram may have only one degree of freedom. In order to secure two degrees of freedom, single-axis rotation is realized so that pitch rotation is realized by the parallelogram, and roll rotation is performed by driving a motor. A typical two degrees of freedom realization device using the parallelogram and the motor has a problem of insufficient precision and rigidity of the corresponding degree of freedom.

Accordingly, Korean Patent Registration No. 10-2502444 provides a surgical device in which pitch and roll modules dependently pitch and roll to form a dual parallelogram by improving the above-described problem.

However, a surgical device capable of more stably and precisely driving the surgical device that forms the dual parallelogram is demanded.

Also, as a medical term, surgery represents a feature of curing diseases by cutting, slitting, or operating a skin, a mucous membrane, or other tissues using a surgical instrument. Particularly, open surgery that cuts and opens a skin of a surgery portion and treats, shapes, or removes organs therein causes a problem such as bleeding, side effects, patient pain, and a scar.

Instead of the open surgery, minimally invasive surgery (MIS) that performs surgery inside by drilling a small insertion hole instead of cutting a skin and inserting a surgical instrument such as an endoscope, a laparoscope, a surgical instrument, or a microsurgical microscope through the insertion hole is in the spotlight. Although the MIS may be performed manually by a surgeon, robotic surgery in which surgery is performed by precisely operating the instrument by using a surgical robot instead of directly operating the instrument by an operator is recently suggested as an alternative method.

In the robotic surgery, a surgical device capable of realizing various surgical operations while maximizing stability during the robotic surgery is demanded.

SUMMARY

The present invention provides a surgical device capable of performing a stable and precise operation and an operation method using the same.

The present invention also provides a surgical device capable of stably realizing various surgical operations and an operation method using the same.

The technical objective of the present invention is not limited to the aforementioned technical problem, and technical problems not mentioned above can be clearly understood by a person skilled in the art by the disclosure below.

An embodiment of the present invention provides a surgical device including a surgical instrument module, a dual parallelogram module connected to a rear side of the surgical instrument module and including a plurality of power transmission units, so that each power transmission unit performs motion driving with two degrees of freedom of pitch and roll driving, and a linear drive module connected to the plurality of power transmission units and linearly driven in one direction to transmit a linear driving force to the dual parallel program module.

In an embodiment of the present invention, a surgical device including a surgical instrument module, a dual parallelogram module connected to a rear side of the surgical instrument module and including a plurality of power transmission units, so that each power transmission unit performs motion driving with two degrees of freedom of pitch and roll driving, and a linear drive module connected to the plurality of power transmission units and linearly driven in one direction to transmit a linear driving force to the dual parallel program module, in which the surgical instrument module includes a holder connected to the plurality of power transmission units and performing a motion driving with the two degrees of freedom, a surgical instrument, and a pre-load part disposed on the holder and rotatably connected to the plurality of power transmission units to press a coupling shaft configured to rotatably connect the holder to the plurality of power transmission units.

In an embodiment of the present invention, a surgical device includes a surgical instrument, a holder supporting the surgical instrument, and a holder drive unit configured to simultaneously guide rotational driving and linear driving of the holder.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Hereinafter, preferred embodiments will be described in detail with reference to the accompanying drawings. Unless otherwise defined, all terms (including technical and scientific terms) used herein have the same meaning as generally understood by those skilled in the art. Terms as defined in a commonly used dictionary should be construed as having the same meaning as in an associated technical context, and unless defined apparently in the description, the terms are not ideally or excessively construed as having formal meaning.

The description of the present invention is intended to be illustrative, and those with ordinary skill in the technical field of the present invention pertains will be understood that the present invention can be carried out in other specific forms without changing the technical idea or essential features.

Figure 1:
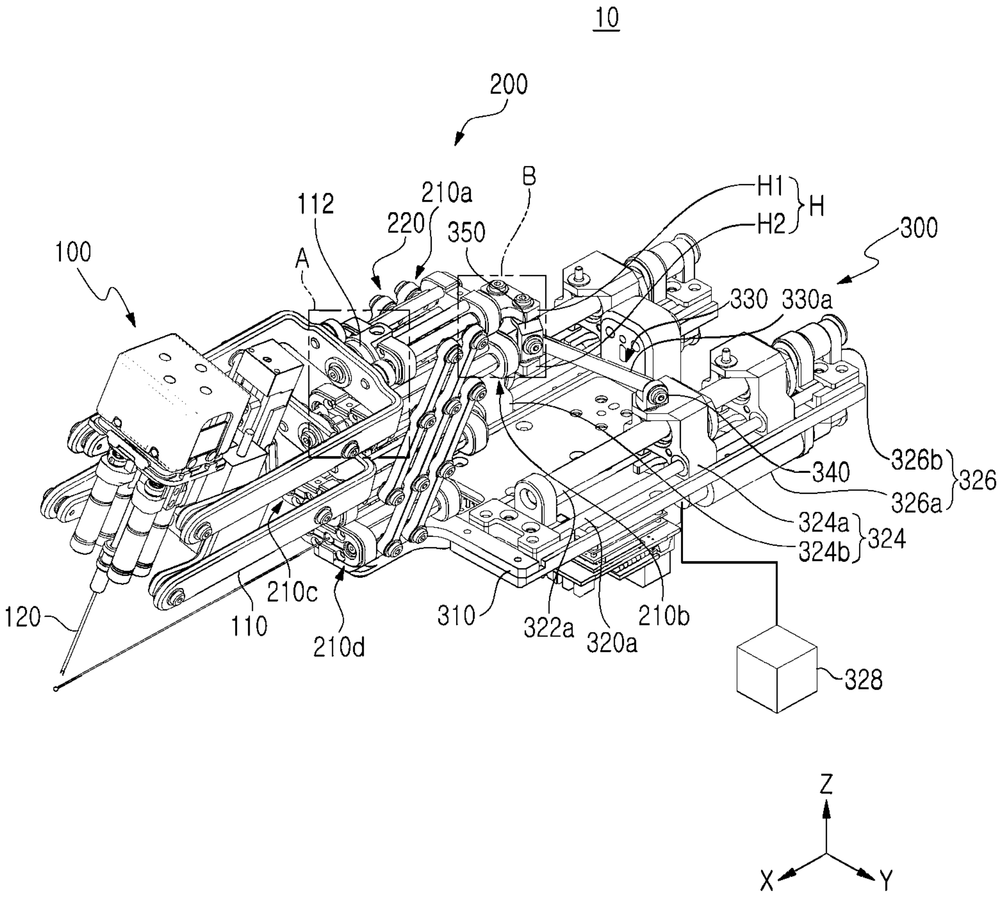
FIG. 1 is a view illustrating a cutting instrument according to an embodiment of the present invention.
Figure 2:
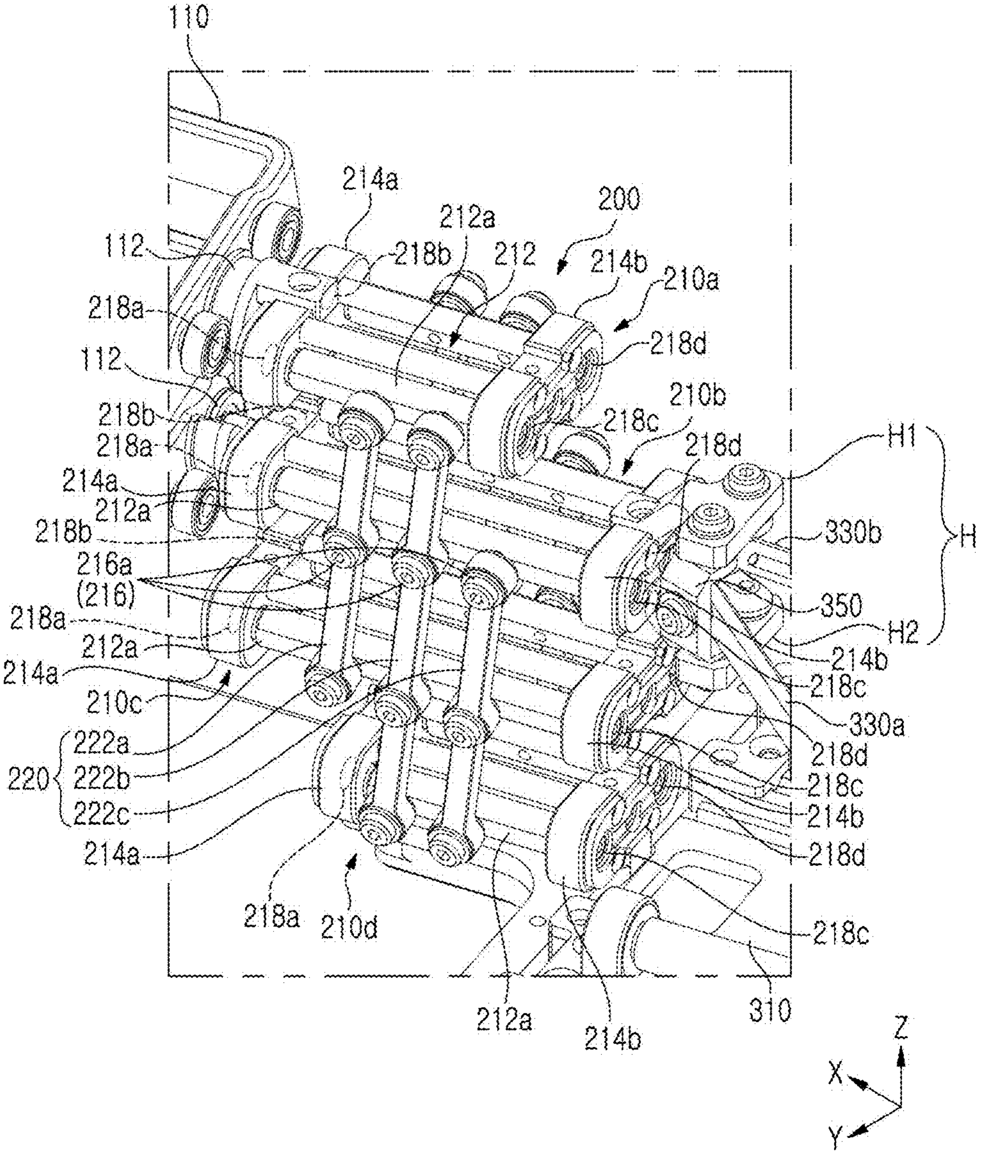
FIGS. 2 and 3 are views for explaining the linear driving of the surgical device 100 of FIG. 1.
Figure 3:
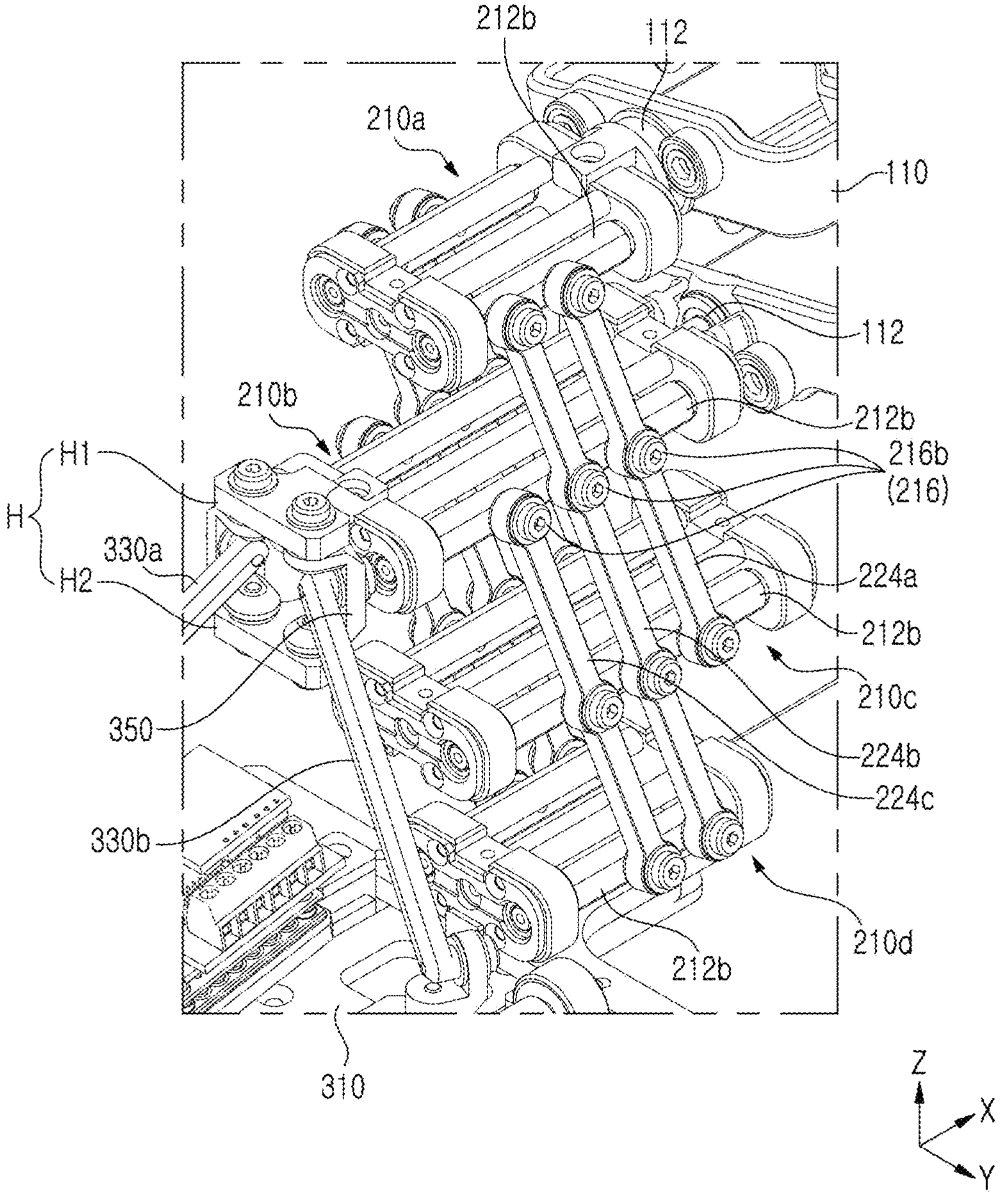

FIG. 1 is a view illustrating a surgical device 10 according to an embodiment of the present invention, and FIGS. 2 and 3 are views illustrating a dual parallelogram module 200 of the surgical device 10 of FIG. 1.

In an embodiment of the present invention, an X-axis direction illustrated in the drawing may be a forward and backward direction of the surgical device 10 that will be described later, a Y-axis direction may be a left and right direction of the surgical device 10 perpendicular to the X-axis direction on a horizontal plane (XY plane), and a Z-axis direction may be a vertical direction perpendicular to both of the X-axis direction and the Y-axis direction.

In the surgical device 10 according to the present invention, a term of roll represents that the surgical device 10 rotates in the left and right direction (rotating around the X-axis), and a term of pitch represents that the surgical device 10 rotates in the forward and backward direction (rotating around the Y-axis).

Referring to FIGS. 1 to 3, the surgical device 10 according to an embodiment of the present invention may include a surgical instrument module 100, a dual parallelogram module 200 and a linear drive module 300. For example, the surgical device 10 may perform surgery on a human body.

The surgical instrument module 100 may include a component (a surgical instrument 120 that will be described later) for gripping a portion (e.g., retina) of the human body.

The dual parallelogram module 200 may be connected to a rear portion of the surgical instrument module 100 and include a plurality of power transmission units 210, so that each of the power transmission units 210 performs a motion driving with two degrees of freedom of pitch and roll driving.

The linear drive module 300 may be connected to the plurality of power transmission units 210 and linearly driven in one direction (forward and backward direction (X-axis direction) of the surgical device 10) to transmit a linear driving force to the dual parallelogram module 200.

Specifically, the plurality of power transmission units 210 of the dual parallelogram module 200 may include a first power transmission unit 210*a*, a second power transmission unit 210*b*, a third power transmission unit 210*c*, and a fourth power transmission unit 210*d*.

Also, the dual parallelogram module 200 may further include a plurality of pitch links 220.

The plurality of pitch links 220 may be spaced a predetermined distance from and parallel to each other in the forward and backward direction (X-axis direction) of the surgical device 10 and jointly connected to the plurality of power transmission units 210, and jointly connect the plurality of power transmission units 210 in the vertical direction of the surgical device 10 to form the dual parallelogram module.

For example, the plurality of pitch links 220 may include a first left pitch link 222*a*, a second left pitch link 222*b*, and a third left pitch link 222*c*. Also, the plurality of pitch links 220 may include a first right pitch link 224*a*, a second right pitch link 224*b*, and a third right pitch link 224*c*.

Also, each of the plurality of power transmission units 210 may include a base link 212, a roll link 214, a pitch joint 216, and a roll joint 218.

The base link 212 may be jointly connected to the plurality of pitch links 220 in the vertical direction of the surgical device 10. The base link 212 may include a left base link 212*a* and a right base link 212*b*.

The roll link 214 may be connected to the base link 212 to roll-rotate. The roll link 214 may include a front base link 214*a* and a rear base link 214*b*.

The pitch joint 216 may jointly connect the base link 212 and the plurality of pitch links 220 to pitch-rotate. The pitch joint 216 may include a left pitch joint 216*a* and a right pitch joint 216*b*.

The roll joint 218 may jointly connect the base link 212 and the roll links 214 to roll-rotate. The roll joint 218 may include a left front roll joint 218*a*, a right front roll joint 218*b*, a left rear roll joint 218*c*, and a right rear roll joint 218*d*.

Here, the terms of left and right may be replaced with other terms depending on a posture position of the dual parallelogram module 200. Although the left base link 212*a* and the right base link 212*b* are separated from each other, the left base link 212*a* and the right base link 212*b* may be integrated with each other as necessary.

Specifically, in the first power transmission unit 210*a*, the left base link 212*a*, the first left pitch link 222*a*, and the second left pitch link 222*b* may be jointly connected to each other at two points to pitch-rotate by the plurality of left pitch joints 216*a*.

Also, in the first power transmission unit 210*a*, the first left pitch link 222*a* and the second left pitch link 222*b* may be spaced a predetermined distance from each other in the forward and backward direction (X-axis direction) of the surgical device 10 and jointly connected to the left base link 212*a*.

Specifically, in the first power transmission unit 210a, the right base link 212b, the first right pitch link 224a, and the second right pitch link 224b may be jointly connected to each other at two points to pitch-rotate by the plurality of right pitch joints 216b.

Also, in the first power transmission unit 210a, the first right pitch link 224a and the second right pitch link 224b may be spaced a predetermined distance from each other in the forward and backward direction (X-axis direction) of the surgical device 10 and jointly connected to the right base link 212b.

Thus, in the first power transmission unit 210a, the base link 212 and the plurality of pitch links 220 may be jointly connected to each other at four points on left and right sides.

Also, in the first power transmission unit 210a, a joint connection of the left base link 212a, the first left pitch link 222a, and the second left pitch link 222b and a joint connection of the right base link 212b, the first right pitch link 224a, and the second right pitch link 224b may be symmetric to each other when viewed from the left and right direction (Y-axis direction) of the surgical device 10.

Also, in the first power transmission unit 210a, the left and right base links 212a and 212b, and the front roll link 214a disposed at a front portion thereof may be jointly connected to each other to roll-rotate by the left and right front roll joints 218a and 218b. Also, the left and right base links 212a and 212b and the rear roll link 214b disposed at a rear portion thereof may be jointly connected to each other to roll-rotate by the left and right rear roll joints 218c and 218d.

According to the embodiment, the first power transmission unit 210a may pitch-rotate around the plurality of left pitch joints 216a and the plurality of right pitch joints 216b. Also, the first power transmission unit 210a may roll-rotate by the front and rear roll links 214a and 214b and the left and right and front and rear roll joints 218a, 218b, 218c, and 218d.

Also, in the second power transmission unit 210b, the left base link 212a and the first left pitch link 222a, the second left pitch link 222b and the third left pitch link 222c may be jointly connected to each other at three points to pitch-rotate by the plurality of left pitch joints 216a.

Also, in the second power transmission unit 210b, the first left pitch link 222a, the second left pitch link 222b, and the third left peach link 222c may be spaced a predetermined distance from each other in the forward and backward direction (X-axis direction) of the surgical device 10 and jointly connected to the left base link 212a at three points.

Also, in the second power transmission unit 210b, the right base link 212b and the first right pitch link 224a and the second right pitch link 224b and the third right pitch link 224c may be jointly connected to each other at three points to pitch-rotate by the plurality of right pitch joint 216b.

Also, in the second power transmission unit 210b, the first left pitch link 224a, the second left pitch link 224b, and the third left peach link 224c may be spaced a predetermined distance from each other in the forward and backward direction (X-axis direction) of the surgical device 10 and jointly connected to the right base link 212b at three points.

Thus, in the second power transmission unit 210a, the base link 212 and the plurality of pitch links 220 may be jointly connected to each other at four points on left and right sides.

Also, in the second power transmission unit 210a, a joint connection of the left base link 212a and the first left pitch link 222a, the second left pitch link 222b, and the third left pitch link 222c and a joint connection of the right base link 212b and the first right pitch link 224a, the second right pitch link 224b, and the third right pitch link 224c may be symmetric to each other when viewed from the left and right direction (Y-axis direction) of the surgical device 10.

Also, in the second power transmission unit 210a, the left and right base links 212a and 212b, and the front roll link 214a disposed at the front portion may be jointly connected to each other to roll-rotate by the left and right front roll joints 218a and 218b. Also, the left and right base links 212a and 212b and the rear roll link 214b disposed at the rear portion may be jointly connected to each other to roll-rotate by the left and right rear roll joints 218c and 218d.

According to the embodiment, the second power transmission unit 210b may pitch-rotate around the plurality of left pitch joints 216a and the plurality of right pitch joints 216b. Also, the second power transmission unit 210a may roll-rotate by the front and rear roll links 214a and 214b and the left and right and front and rear roll joints 218a, 218b, 218c, and 218d.

Also, in the third power transmission unit 210c, the left base link 212a and the first left pitch link 222a, the second left pitch link 222b, and the third left pitch link 222c may be jointly connected to each other at three points to pitch-rotate by the plurality of left pitch joints 216a.

Also, in the third power transmission unit 210c, the first left pitch link 222a, the second left pitch link 222b, and the third left peach link 222c may be spaced a predetermined distance from each other in the forward and backward direction (X-axis direction) of the surgical device 10 and jointly connected to the left base link 212a at three points.

Also, in the third power transmission unit 210c, the right base link 212b and the first right pitch link 224a, the second right pitch link 224b, and the third right pitch link 224c may be jointly connected to each other at three points to pitch-rotate by the plurality of right pitch joints 216b.

Also, in the third power transmission unit 210c, the first right pitch link 224a, the second right pitch link 224b, and the third right peach link 224c may be spaced a predetermined distance from each other in the forward and backward direction (X-axis direction) of the surgical device 10 and jointly connected to the right base link 212b at three points.

Thus, in the third power transmission unit 210c, the base link 212 and the plurality of pitch links 220 may be jointly connected to each other at six points on left and right sides.

Also, in the third power transmission unit 210a, a joint connection of the left base link 212a and the first left pitch link 222a, the second left pitch link 222b, and the third left pitch link 222c and a joint connection of the right base link 212b and the first right pitch link 224a, the second right pitch link 224b, and the third right pitch link 224c may be symmetric to each other when viewed from the left and right direction (Y-axis direction) of the surgical device 10.

Also, in the third power transmission unit 210a, the left and right base links 212a and 212b, and the front roll link 214a disposed at the front portion may be jointly connected to each other to roll-rotate by the left and right front roll joints 218a and 218b. Also, the left and right base links 212a and 212b and the rear roll link 214b disposed at the rear portion may be jointly connected to each other to roll-rotate by the left and right rear roll joints 218c and 218d.

According to the embodiment, the third power transmission unit 210c may pitch-rotate around the plurality of left pitch joints 216a and the plurality of right pitch joints 216b. Also, the third power transmission unit 210c may roll-rotate by the front and rear roll links 214a and 214b and the left and right and front and rear roll joints 218a, 218b, 218c, and 218d.

Also, in the fourth power transmission unit 210*d*, the left base link 212*a*, the first left pitch link 222*a*, and the second left pitch link 222*b* may be jointly connected to each other at two point to pitch-rotate by the plurality of left pitch joints 216*a*.

Also, in the fourth power transmission unit 210*d*, the first left pitch link 222*a* and the second left pitch link 222*b* may be spaced a predetermined distance from each other in the forward and backward direction (X-axis direction) of the surgical device 10 and jointly connected to the left base link 212*a*.

Also, in the fourth power transmission unit 210*d*, the right base link 212*b*, the first right pitch link 224*a*, and the second right pitch link 224*b* may be jointly connected to each other at two points to pitch-rotate by the plurality of right pitch joints 216*b*.

Also, in the fourth power transmission unit 210*d*, the first right pitch link 224*a* and the second right pitch link 224*b* may be spaced a predetermined distance from each other in the forward and backward direction (X-axis direction) of the surgical device 10 and jointly connected to the right base link 212*b*.

Thus, in the fourth power transmission unit 210*d*, the base link 212 and the plurality of pitch links 220 may be jointly connected to each other at six points on left and right sides.

Also, in the fourth power transmission unit 210*d*, a joint connection of the left base link 212*a* and the first and second left pitch links 222*a* and 222*b* and a joint connection of the right base link 212*b* and the first and second right pitch links 224*a* and 224*b* may be symmetric to each other when viewed from the left and right direction (Y-axis direction) of the surgical device 10.

Also, in the fourth power transmission unit 210*d*, the left and right base links 212*a* and 212*b* and the front roll link 214*a* disposed at the front portion may be jointly connected to each other to roll-rotate by the left and right front roll joints 218*a* and 218*b*. Also, the left and right base links 212*a* and 212*b* and the rear roll link 214*b* disposed at the rear portion may be jointly connected to each other to roll-rotate by the left and right rear roll joints 218*c* and 218*d*.

According to the embodiment, the fourth power transmission unit 210*d* may pitch-rotate around the plurality of left pitch joints 216*a* and the plurality of right pitch joints 216*b*. Also, the fourth power transmission unit 210*d* may be roll-rotated by the front and rear roll links 214*a* and 214*b* and the left and right and front and rear roll joints 218*a*, 218*b*, 218*c*, and 218*d*.

In FIGS. 2 and 3, the first power transmission unit 210*a* may be disposed at an uppermost portion, and the second power transmission unit 210*b*, the third power transmission unit 210*c*, and the fourth power transmission unit 210*d* may be sequentially arranged in a stage type in the vertical direction. Also, the first left pitch link 222*a*, the second left pitch link 222*b* and the third left pitch link 222*c* may jointly connect left sides of the first to fourth power transmission units 210*a*, 210*b*, 210*c*, and 210*d* in the vertical direction. Also, the first right pitch link 224*a*, the second right pitch link 224*b*, and the third right pitch link 224*c* may jointly connect right sides of the first to fourth power transmission units 210*a*, 210*b*, 210*c*, and 210*d* in the vertical direction.

Also, the first to third pitch links 222*a*, 222*b*, and 222*c* and the first to third right pitch links 224*a*, 224*b*, and 224*c* may be symmetric to each other when viewed in the left and right direction of the surgical device 10 and jointly connected to the first to fourth power transmission units 210*a*, 210*b*, 210*c*, and 210*d*.

When joint points of each of the plurality of left pitch joints 216*a* in the first transmission unit 210*a*, the plurality of left pitch joints 216*a* in the second power transmission unit 210*b*, the plurality of left pitch joints 216*a* in the third power transmission unit 210*c*, and the plurality of left pitch joints 216*a* in the fourth power transmission unit 210*d* are connected in the vertical direction, three virtual vertical lines may be spaced a predetermined distance from and parallel to each other. Also, right sides of the first to fourth power transmission units 210*a*, 210*b*, 210*c*, and 210*d* may form three virtual vertical lines that are spaced a predetermined distance from and parallel to each other.

When the joint points of each of the plurality of left pitch joints 216*a* in the first transmission unit 210*a*, the plurality of left pitch joints 216*a* in the second power transmission unit 210*b*, the plurality of left pitch joints 216*a* in the third power transmission unit 210*c*, and the plurality of left pitch joints 216*a* in the fourth power transmission unit 210*d* are connected in the forward and backward direction (X-axis direction) of the surgical device 10, four virtual vertical lines may be spaced a predetermined distance from and parallel to each other. Also, right sides of the first to fourth power transmission units 210*a*, 210*b*, 210*c*, and 210*d* may form four virtual vertical lines that are spaced a predetermined distance from and parallel to each other.

Also, the first power transmission unit 210*a* and the fourth power transmission unit 210*d* may be jointly connected to the plurality of pitch links 220 at two points in the forward and backward direction of the surgical device 10. Here, the two-point joint connection of the first power transmission unit 210*a* and the fourth power transmission unit 210*d* may be connected such that one joint connection point meets each other on a virtual vertical line. Also, the second power transmission unit 210*b* and the third power transmission unit 210*c* may be joint-connected to the plurality of pitch links 220 at three points in the forward and backward direction of the surgical device 10. Here, the dual parallelogram module 200 may form a dual parallelogram when connecting each joint connection point in the forward and backward direction (X-axis direction) and the vertical direction of the surgical device 10.

As the linear drive module 300 that is linearly driven in the forward and backward direction (X-axis direction) of the surgical device 10 is coupled to the dual parallelogram module 200 having the above-described configuration, a driving force for the dual parallelogram module 200 to perform a motion driving of two degrees of freedom of pitch and roll driving may be provided through driving of the linear drive module 300.

According to the above-described embodiment of the present invention, since the motion driving of the surgical instrument module 100 with two degrees of freedom may be realized through the dual parallelogram module 200 by transmitting the linear driving force to the dual parallelogram module 200, the surgical instrument module 100 may be further precisely driven than a method of driving the dual parallelogram module 200 simply through a rotational driving force. Thus, more precise surgery may be performed by the surgical instrument module 100, and a safety accident occurring during surgery may be prevented through precise driving of the surgical instrument module 100.

Referring to FIG. 1, the surgical instrument module 100 may include a holder 110 and a surgical instrument 120.

The holder 110 may constitute an appearance of the surgical instrument module 100. Also, the holder 110 may be connected to the plurality of power transmission units 210 to perform the motion driving with the two degrees of freedom.

That is, the holder 110 may perform the motion driving with the two degrees of freedom of pitch or roll driving according to the driving of the plurality of power transmission units 210. For example, the holder 110 may be connected to the first power transmission unit 210*a* and the second power transmission unit 210*b* among the plurality of power transmission units 210.

The surgical instrument 120 may be supported by the holder 110. For example, the surgical instrument 120 may include a gripping unit having a forceps-shape at an end thereof to grip a portion of the human body.

That is, when the holder 110 is pitched or rolled according to the driving of the plurality of power transmission units 210, the surgical instrument 120 may be pitched or rolled in conjunction with the driving of the holder 110.

Figure 4:
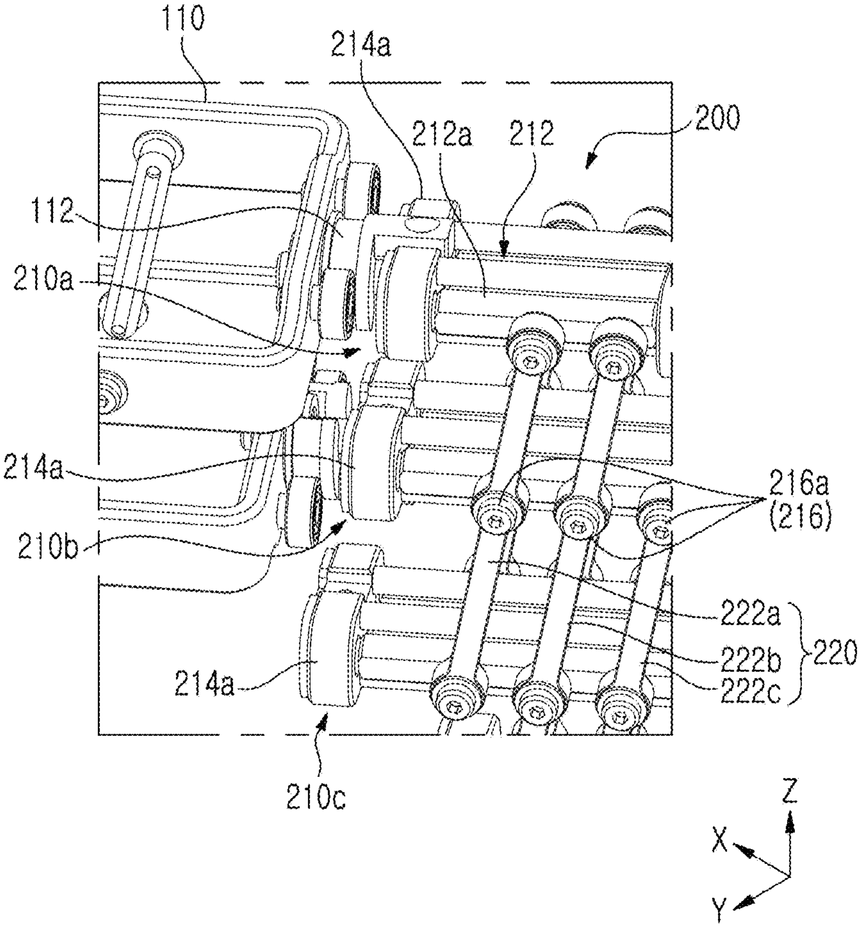
FIG. 4 is an enlarged view illustrating portion A of FIG. 1.

FIG. 4 is an enlarged view illustrating portion A of FIG. 1.

Referring to FIG. 4, the holder 110 may further include a rotation bearing 112. The rotation bearing 112 may be rotatably connected to the plurality of power transmission units 210.

Specifically, the rotation bearing 112 may be connected to the first power transmission unit 210*a* and the second power transmission unit 210*b* among the plurality of power transmission units 210.

Thus, the motion driving force with the two degrees of freedom according to the driving of the dual parallelogram module 200 may be easily transmitted to the surgical instrument module 100.

Also, the linear drive module 300 may include a module body 310, a linear drive unit 320, and a link 330.

The module body 310 may constitute an appearance of the linear drive module 300.

The linear drive unit 320 may be disposed on the module body 310 and linearly driven along the forward and backward direction (X-axis direction) of the module body 310.

The link 330 may have one end rotatably connected to the linear drive unit 320 and the other end rotatably connected to the plurality of power transmission units 210. In an embodiment, the link 330 may be connected to the second power transmission unit 210*b* connected to the holder 110 among the plurality of power transmission units 210.

As described above, since the linear driving force of the linear drive unit 320 may be transmitted to the dual parallelogram module 200 through the link 330 configured to rotate with respect to both the linear drive unit 320 and the power transmission unit 210, the motion driving force of the two degrees of freedom according to the driving of the dual parallelogram module 200 may be easily transmitted to the surgical instrument module 100. Thus, more precise surgery may be performed by the surgical instrument module 100.

As illustrated in FIG. 1, the linear drive unit 320 and the link 330 may be provided in pair in the left and right direction (Y-axis direction) of the module body 310.

Specifically, the linear drive unit 320 may include a first linear drive unit 320*a* disposed at a left side of the module body 310 and a second linear drive unit 320*b* disposed at a right side of the module body 310.

Also, the link 330 may include a first link 330*a* and a second link 330*b*.

The first link 330*a* may have one end rotatably connected to the first linear drive unit 320*a* and the other end may be rotatably connected to the second power transmission unit 210*b*.

The second link 330*b* may have one end rotatably connected to the second linear drive unit 320*b* and the other end rotatably connected to the second power transmission unit 210*b*.

As described above, since the linear drive unit 320 generating the linear driving force and the link 330 rotatably connected to each of the linear drive unit 320 and the power transmission unit 210 are provided in pair, the pitch and roll driving performed by the dual parallelogram module 200 may be further stably performed.

Specifically, the linear drive unit 320 may include a guide rail 322 and a moving block 324.

The guide rail 322 may extend along the forward and backward direction (X-axis direction) of the module body 310.

Specifically, the guide rail 322 may include a first rail 322*a* disposed at the left side of the module body 310 and a second rail 322*b* disposed at the right side of the module body 310.

One end of the link 330 may be rotatably connected to the moving block 324, and the moving block 324 may be linearly driven along a guide rail 322 in the forward and backward direction (X-axis direction) of the module body 310.

Specifically, the moving block 324 may include a first block 324*a* and a second block 324*b*.

One end of the first link 330*a* may be rotatably connected to the first moving block 324*a*, and the first moving block 324 may be linearly driven along a first guide rail 322*a* in the forward and backward direction (X-axis direction) of the module body 310.

One end of the first link 330*a* may be rotatably connected to the first moving block 324*a*, and the first moving block 324 may be linearly driven along a first guide rail 322*a* in the forward and backward direction (X-axis direction) of the module body 310.

Also, the linear drive module 300 may further include a first pivot joint 340.

The first pivot joint 340 may have a lower side rotatably connected to the moving block 324. Also, the first pivot joint 340 may have a side surface to which one end of the link 330 is rotatably connected.

The first pivot joints 340 may be provided in pair in the left and right direction (Y-axis direction) of the module body 310.

According to the embodiment, since the first pivot joint 340 supporting the link 330 rotatably with respect to the moving block 324 may be rotatably connected to the moving block 324 linearly driven along the guide rail 322, the motion driving may be performed more various methods by the link 330 when the linear driving force of the linear drive unit 320 is transmitted to the line unit 330 and converted into the rotational driving force. Accordingly, the pitch and roll driving by the dual parallelogram module 200 may be more stably performed.

Figure 5:
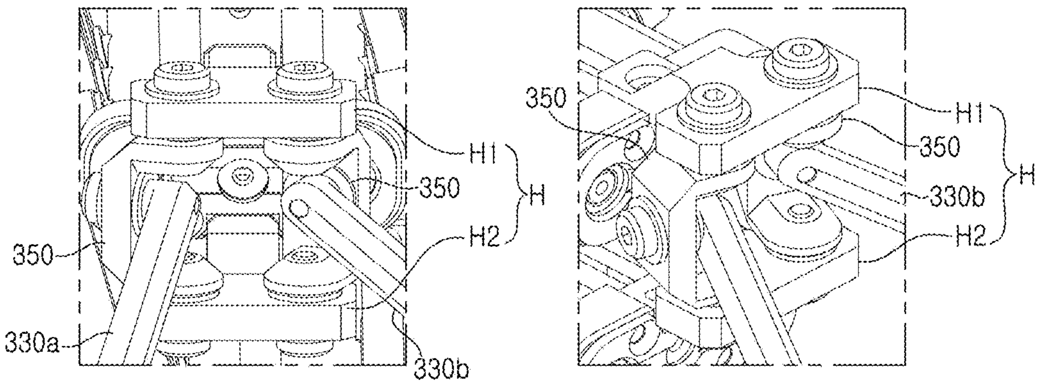
FIG. 5 is an enlarged view illustrating portion B of FIG. 1.

FIG. 5 is an enlarged view illustrating portion B of FIG. 1.

Referring to FIGS. 1 and 5, one of the plurality of power transmission units 210 may include a support unit H. Here, the second power transmission unit 210*b* may include the support unit H.

The support unit H may support the other end of the link 330.

Also, the linear drive module 300 may further include a second pivot joint 350.

The second pivot joint 350 may be rotatably coupled to the support unit H. Also, the other end of the link 330 may be rotatably connected to the second pivot joint 350.

Specifically, the support unit H may have an upper surface H1 and a lower surface H2.

The upper surface H1 may extend from the second power transmission unit 210*b* in the forward and backward direction (X-axis direction) of the surgical device 10.

The lower surface H2 may be disposed opposite to the upper surface H1 in the vertical direction and extend from the second power transmission unit 210*b* in the forward and backward direction (X-axis direction) of the surgical device 10.

The second pivot joint 350 may be provided in pair in the left and right direction (Y-axis direction) of the support unit H.

Here, upper and lower ends of a pair of second pivot joints 350 may be rotatably coupled to the upper and lower surfaces H1 and H2 of the support unit H, respectively.

Also, the other end of the first link 330*a* may be rotatably connected to the second pivot joint 350 on the left, and the other end of the second link 330*b* may be rotatably connected to the second pivot joint 350 on the right.

According to the embodiment, since the second pivot joint 350 supporting the link 330 rotatably with respect to the power transmission unit 210 may be rotatably connected to the support unit H of the transmission unit 210, the motion driving may be performed in various methods by the link 330 when the linear driving force of the linear drive unit 320 may be transmitted to the link 330 and converted into the rotational driving force. Accordingly, the pitch and roll driving by the dual parallelogram module 200 may be more stably performed.

Referring to FIG. 5, the second pivot joint 350 may surround a portion of the other end of the link 330.

Specifically, as illustrated in FIG. 5, the second pivot joint 350 may surround the other end of the link 330 through the upper surface, the lower surface, and one side surface connecting the upper and lower surfaces.

Also, the other end of the link 330 may be rotatably coupled to the side surface of the second pivot joint 350.

Specifically, as illustrated in FIG. 5, the other end of the link 330 may be rotatably coupled to one side surface of the second pivot joint joint 350, which connects the upper surface and the lower surface of the second pivot joint 350.

According to the embodiment, since the other end of the link 330 connected closer to the surgical instrument module 100 than one end of the link 330 in the dual parallelogram module 200 may be more stably connected to the power transmission unit 210, the pitch and roll driving performed by the dual parallelogram module 200 may be more stably performed, and precision of the driving of the surgical instrument module 100 may be more reliably secured.

On the other hand, the power transmission unit 210 disposed at the lowermost among the plurality of power transmission units 210 may be connected to the module body 310.

Specifically, as illustrated in FIG. 1, the fourth power transmission unit 210*d* may be coupled to a lower side of the module body 310.

According to the embodiment, since the motion driving with the two degrees of freedom may be performed in a state in which the lower side of the dual parallelogram module 200 is supported by the linear drive module 300, the pitch and roll driving performed by the dual parallelogram module 200 may be more stably performed.

Hereinafter, based on the above-described configuration of the surgical device 10, the pitch and roll driving of the surgical device 10 will be described in detail with reference to FIGS. 6 to 9.

Figure 6:
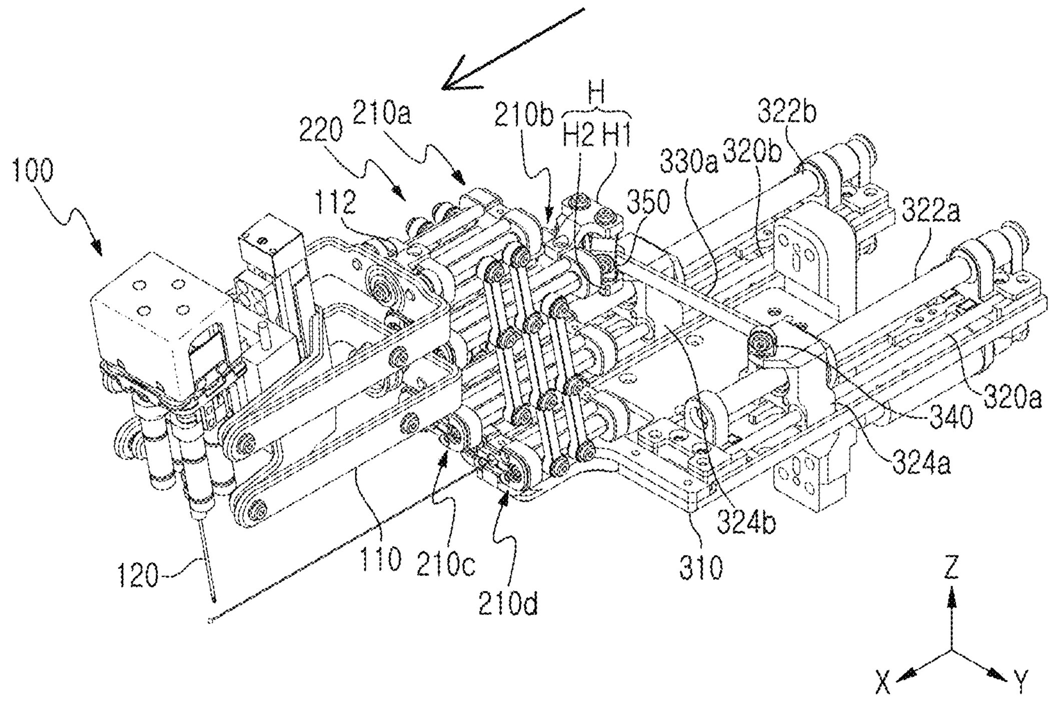
FIG. 6 is a view illustrating a first driving example of the surgical device of FIG. 1.

FIG. 6 is a view illustrating a first driving example of the surgical device 10 of FIG. 1.

Referring to FIG. 6, when all of the pair of linear drive units 320 are linearly driven in a forward direction of the module body 310, the surgical instrument module 100 may be pitched in the forward direction.

Specifically, as illustrated in FIG. 6, the first block 324*a* is linearly driven in the forward direction of the module body 310 along the first rail 322*a*, and the second block 324*b* is linearly driven in the forward direction of the module body 310 along the second rail 322*b*, the first link 330*a* and the second link 330*b* connected to the first block 324*a* and the second block 324*b*, respectively, are moved in the forward direction of the module body 310. Accordingly, as the entire dual parallelogram module 200 is moved in the forward direction, the surgical instrument module 100 may be pitched in the forward direction.

Figure 7:
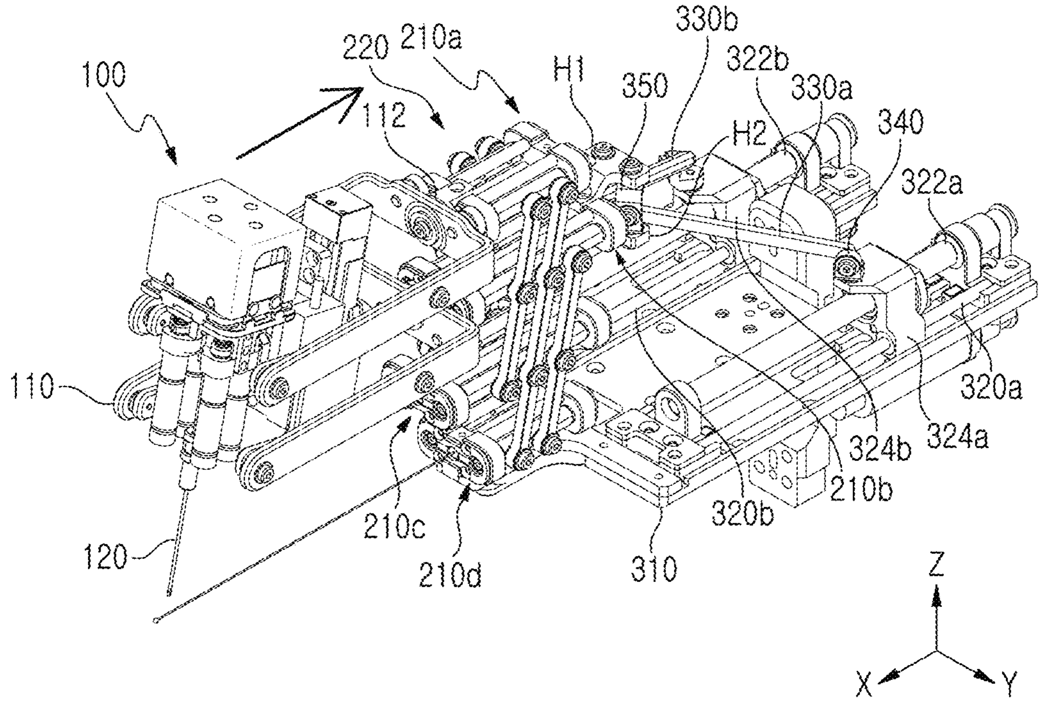
FIG. 7 is a view illustrating a second driving example of the surgical device of FIG. 1.

FIG. 7 is a view illustrating a second driving example of the surgical device 10 of FIG. 1.

Referring to FIG. 7, when all of the pair of linear drive units 320 are linearly driven in a backward direction of the module body 310, the surgical instrument module 100 may be pitched in the backward direction.

Specifically, as illustrated in FIG. 7, the first block 324*a* is linearly driven in the backward direction of the module body 310 along the first rail 322*a*, and the second block 324*b* is linearly driven in the backward direction of the module body 310 along the second rail 322*b*, the first link 330*a* and the second link 330*b* connected to the first block 324*a* and the second block 324*b*, respectively, may be moved in the backward direction of the module body 310. Accordingly, as the entire dual parallelogram module 200 is moved in the backward direction, the surgical instrument module 100 may be pitched in the backward direction.

Figure 8:
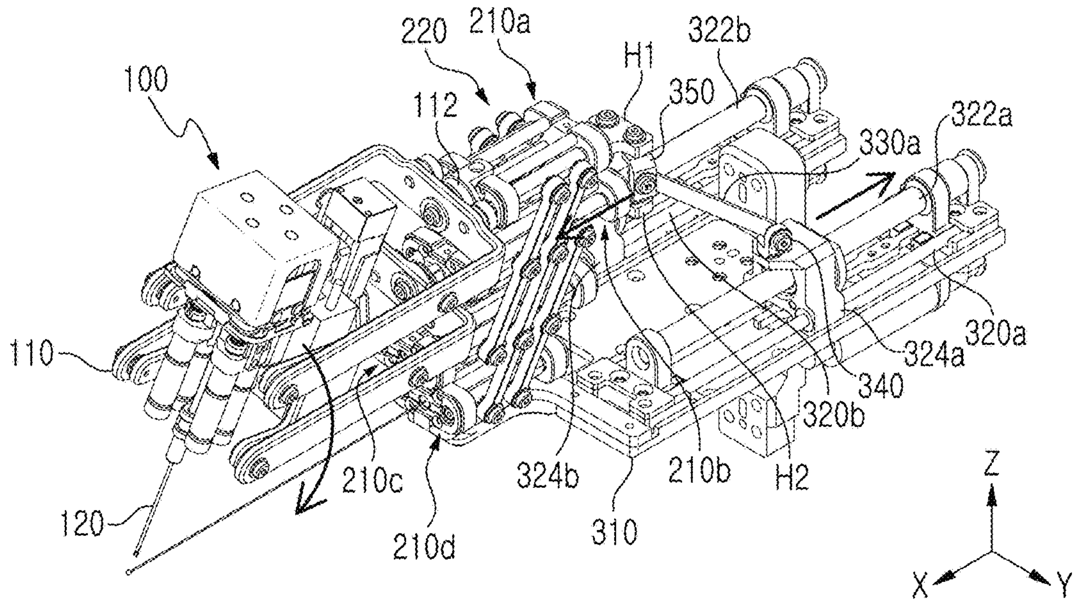
FIG. 8 is a view illustrating a third driving example of the surgical device of FIG. 1.
Figure 9:
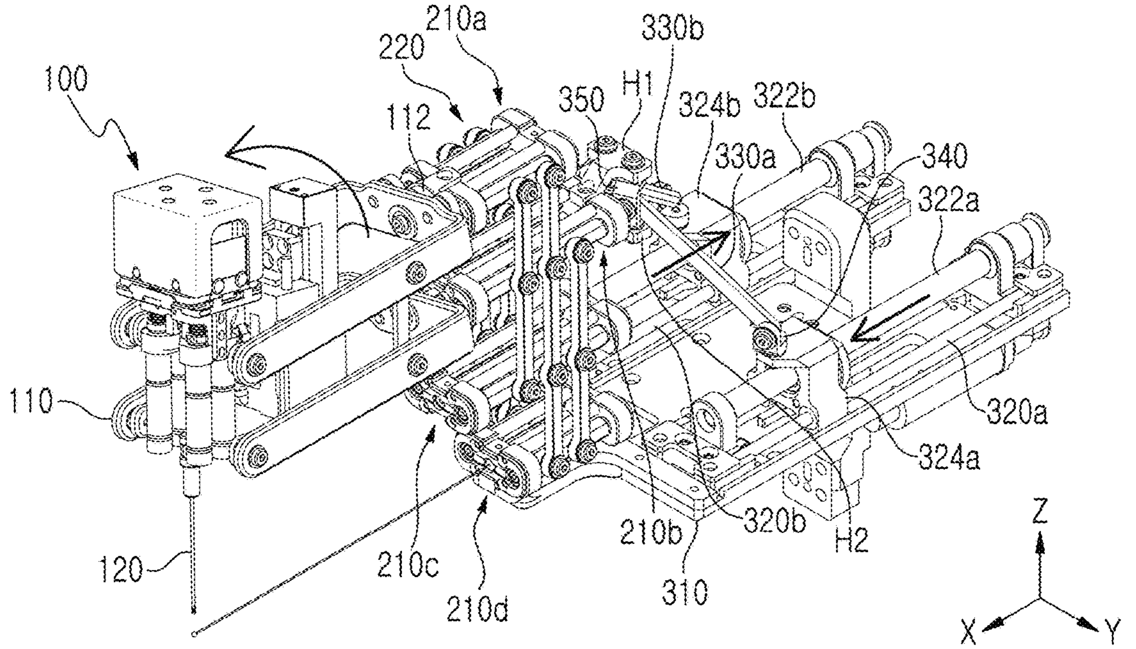
FIG. 9 is a view illustrating a fourth driving example of the surgical device of FIG. 1.

FIG. 8 is a view illustrating a third driving example of the surgical device 1 of FIG. 1, and FIG. 9 is a view illustrating a fourth driving example of the surgical device 1 of FIG. 1. Here, FIG. 8 is a view illustrating a state in which the surgical instrument module 100 is rolled to the left, and FIG. 9 is a view illustrating a state in which the surgical instrument module 100 is rolled to the right.

Referring to FIGS. 8 and 9, when one of the pair of linear drive units 320 is linearly driven in the forward direction of the module body 310, and the other of the pair of linear drive units 320 is linearly driven in the backward direction of the module body 310, the surgical instrument module 100 may be rolled to the left or right.

Specifically, as illustrated in FIG. 8, the first block 324*a* is linearly driven in the backward direction of the module body 310 along the first rail 322*a*, and the second block 324*b* is linearly driven in the forward direction of the module body 310 along the second rail 322*b*, the first link 330*a* connected to the first block 324*a* may be moved in the backward direction of the module body 310, and the second block 324*b* connected to the second block 324*b* may be moved in the forward direction of the module body 310. Accordingly, as the entire dual parallelogram module 200 is moved in the left direction, the surgical instrument module 100 may be rolled in the left direction.

Specifically, as illustrated in FIG. 9, the first block 324*a* is linearly driven in the forward direction of the module body 310 along the first rail 322*a*, and the second block 324*b* is linearly driven in the backward direction of the module body 310 along the second rail 322*b*, the first link 330*a* connected to the first block 324*a* may be moved in the forward direction of the module body 310, and the second block 324*b* connected to the second block 324*b* may be moved in the backward direction of the module body 310. Accordingly, as the entire dual parallelogram module 200 is moved in the right direction, the surgical instrument module 100 may be rolled in the right direction.

In an embodiment, a rotation angle in the above-described roll driving may be determined according to a difference between a displacement in the forward direction of one module body 310 of the pair of linear drive units 320 and a displacement in the backward direction of the other module body 310 of the pair of linear drive units 320.

Specifically, as illustrated in FIG. 8, the rotation angle by which the surgical instrument module 100 is rolled to the left may be varied according to the displacement by which the first block 324*a* is linearly driven in the backward direction of the module body 310 along the first rail 322*a* and the displacement by which the second block 324*b* is linearly driven in the forward direction of the module body 310 along the second rail 322*b*.

Also, as illustrated in FIG. 9, the rotation angle by which the surgical instrument module 100 is rolled in the backward direction may be varied according to the displacement by which the first block 324*a* is linearly driven in the forward direction of the module body 310 along the first rail 322*a* and the displacement by which the second block 324*b* is linearly driven in the backward direction of the module body 310 along the second rail 322*b*.

Figure 10:
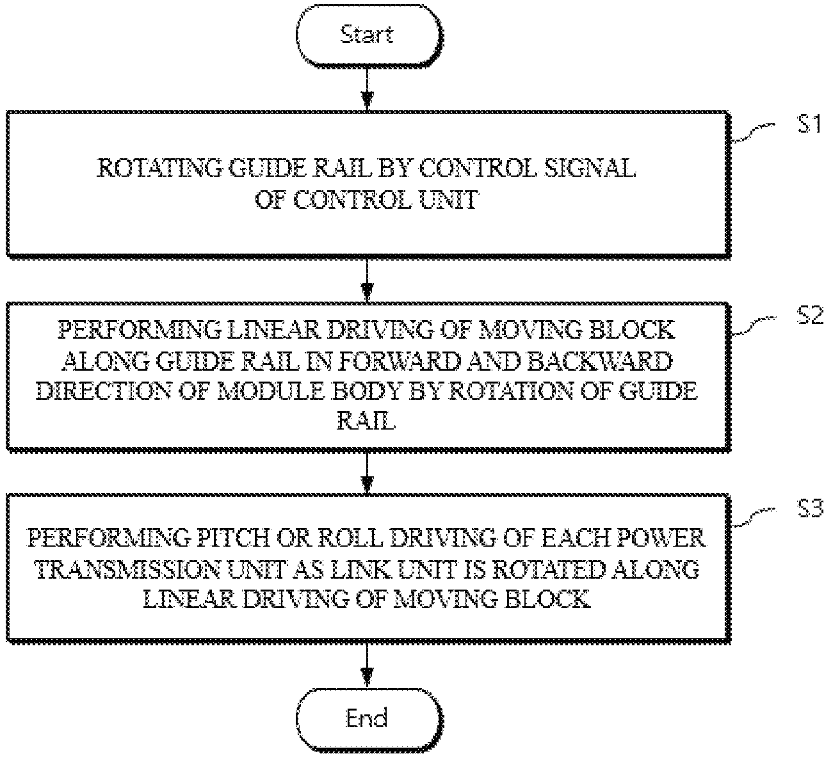
FIG. 10 is a flowchart representing a method of operating a surgical device by using the surgical device of FIG. 1.

FIG. 10 is a flowchart representing a method of operating a surgical device by using the surgical device 10 of FIG. 1.

Referring to FIG. 10 together with FIGS. 1 to 9, the method of operating the surgical device according to an embodiment of the present invention may include steps S1 to S3 as stated below.

In the step S1, the guide rail 322 is rotated by a control signal of a control unit 328. Here, the above-described linear drive unit 320 may include the control unit 328. For example, the control unit 328 may include a processor. Here, the processor may be realized into CPU, GPU, AP, each of which has a calculation function or a combination thereof, and provided together with various types of memories such as DRAM, a flash memory, and SSD as necessary. The control unit 328 may control the surgical instrument module 100 to perform the motion driving with two degrees of freedom of the pitch and roll driving according to a command input by a user.

Specifically, the linear drive unit 320 may include a driving force providing unit 326 that rotates the guide rail 322 according to the control signal of the control unit 328. Here, the guide rail 322 may be a lead screw. However, the embodiment of the present invention is not limited thereto.

More specifically, the driving force providing unit 326 may include a motor 326*a* and a drive belt 326*b*.

As illustrated in FIG. 1, the motor 326*a* may be disposed at a lower portion of the module body 310. Also, the motor 326*a* may be driven according to the control signal of the control unit 328.

The drive belt 326*b* may be rotatably supported by one end of the guide rail 322 disposed at an upper portion of the module body 310 as illustrated in FIG. 1. Also, the drive belt 326*b* may be rotatably supported by one end of the motor 326*a* disposed at the lower portion of the module body 310. Thus, when the motor 326*a* is rotated according to the control signal of the control unit 328, as the drive belt 326*b* supported by the motor 326*a* is rotated, the guide rail 322 supporting the drive belt 326*b* may be also rotated by the rotational driving force of the motor 326*a* transmitted from the drive belt 326*b*.

In the step S2, the moving block 324 is linearly driven along the guide rail 322 in the forward and backward direction of the module body 310 by the rotation of the guide rail 322. Here, the above-described driving force providing unit 326 may be disposed at the lower portion of the module body 310 in correspondence to each of the first rail 322*a* and the second rail 322*b*. Also, the driving force providing units 326 may drive the first rail 322*a* and the second rail 322*b* in the same direction or in opposite directions when viewed from the forward and backward direction of the module body 310. Accordingly, the first block 324*a* and the second block 324*b* may be also driven in the same direction or in opposite directions when viewed from the forward and backward direction of the module body 310.

In the step S3, as the moving block 324 is linearly driven, the link 330 is rotated, and each power transmission unit 210 is pitched or rolled. Here, the link 330 may be more easily rotated by the first pivot joint 340 and the second pivot joint 350 connected to the link 330.

As described above, each of the guide rail 322, the moving block 324, and the link 330 may be provided in pair in the left and right direction of the module body 310.

Here, the step S3 may include a step of pitching the surgical instrument module 100 in the forward direction when all of the pair of moving blocks 324 are linearly driven in the forward direction of the module body 310 and a step of pitching the surgical instrument module 100 in the backward direction when all of the pair of moving blocks 324 are linearly driven in the backward direction of the module body 310.

Also, the step S3 may further include a step of rolling the surgical instrument module 100 to the left or right when one of the pair of moving blocks 324 is linearly driven in the forward direction of the module body 310, and the other of the pair of moving blocks 324 is linearly driven in the backward direction of the module body 310.

Figure 11:
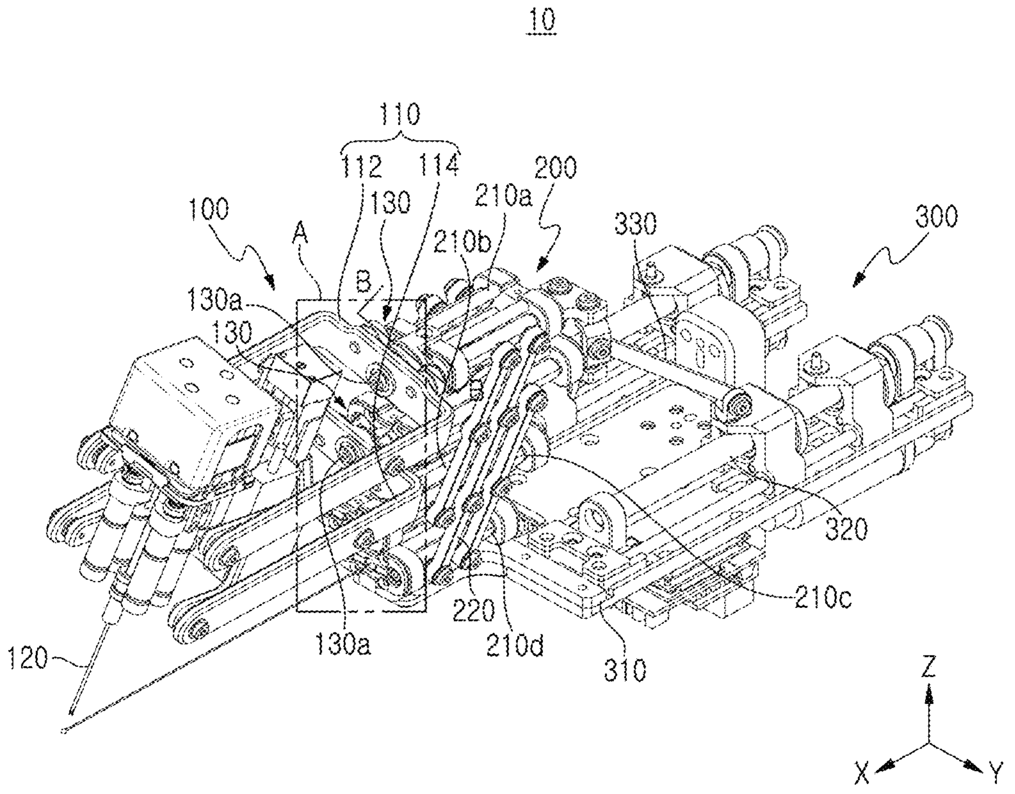
FIG. 11 is a view illustrating an example of the surgical device according to an embodiment of the present invention.
Figure 12:
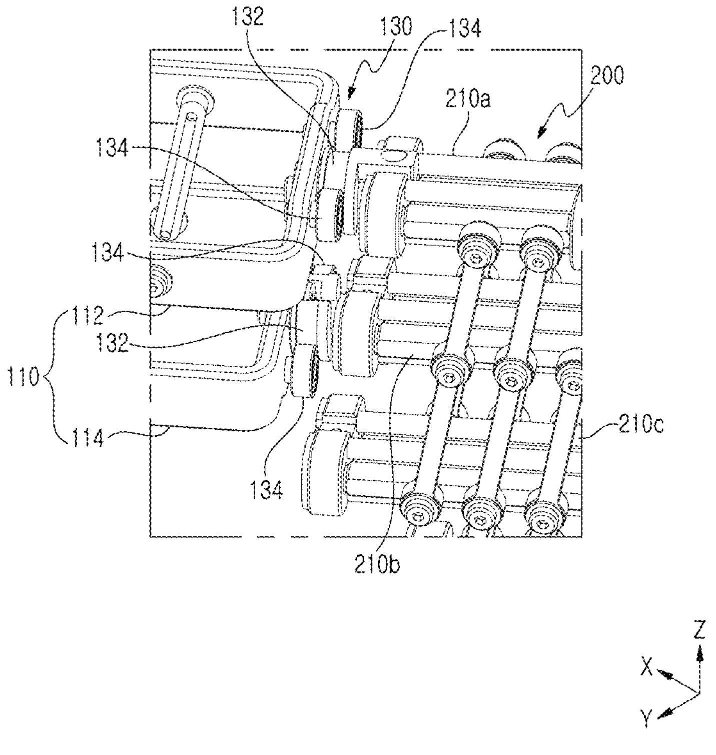
FIG. 12 is an enlarged view illustrating portion A of FIG. 11.
Figure 13:
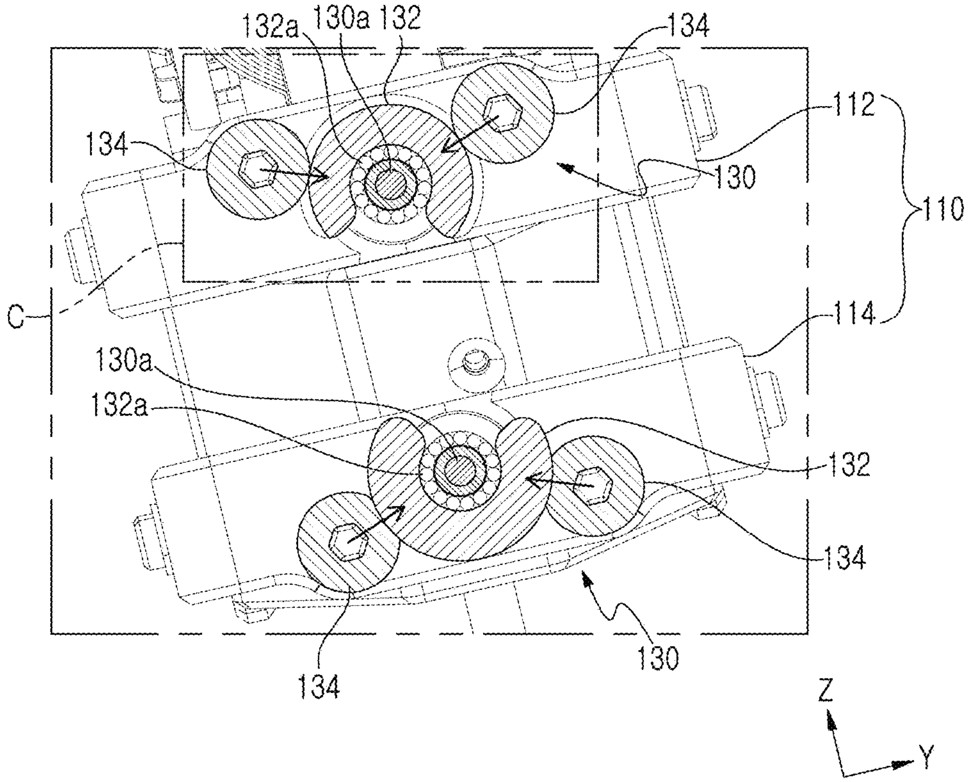
FIG. 13 is a cross-sectional view taken along line B-B' of FIG. 12.
Figure 14:
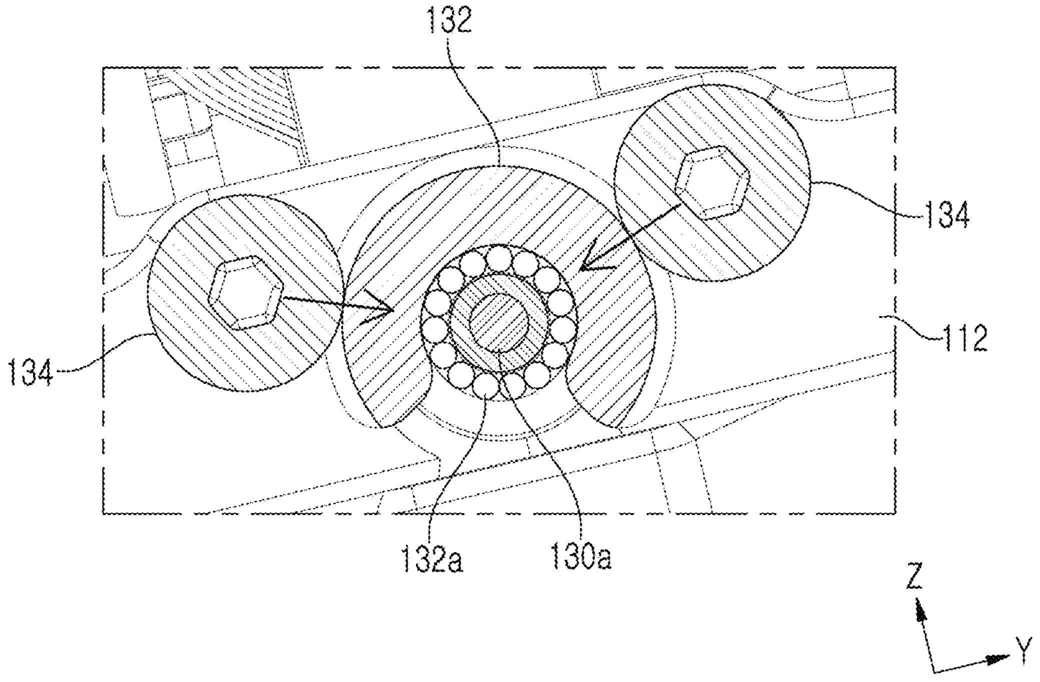
FIG. 14 is an enlarged view illustrating portion C of FIG. 13.

FIG. 11 is a view illustrating an example of the surgical device according to the present invention, FIG. 12 is an enlarged view illustrating portion A of FIG. 11, FIG. 13 is a cross-sectional view taken along line B-B' of FIG. 11, and FIG. 14 is an enlarged view illustrating portion C of FIG. 13.

Referring to FIGS. 11 to 14, the surgical device 10 according to an embodiment of the present invention may include a surgical instrument module 100, a dual parallelogram module 200 and a linear drive module 300. For example, the surgical device 10 may perform surgery on a human body.

Specifically, the surgical instrument module 100 may include a holder 110, a surgical instrument 120, and a pre-load part 130.

The holder 110 may constitute an appearance of the surgical instrument module 100. Also, the holder 110 may be connected to a plurality of power transmission units 210 to perform a motion driving with two degrees of freedom.

That is, the holder 110 may perform the motion driving with the two degrees of freedom of pitch or roll driving according to the driving of the plurality of power transmission units 210. For example, the holder 110 may be connected to the first power transmission unit 210*a* and the second power transmission unit 210*b* among the plurality of power transmission units 210.

The surgical instrument 120 may be supported by the holder 110. For example, the surgical instrument 120 may include a gripping unit having a forceps-shape at an end thereof to grip a portion of the human body.

That is, when the holder 110 is pitched or rolled according to the driving of the plurality of power transmission units 210, the surgical instrument 120 may be pitched or rolled in conjunction with the driving of the holder 110.

The pre-load part 130 may be disposed on the holder 110 and rotatably connected to the plurality of power transmission units 210. Also, the pre-load part 130 may press a coupling shaft 130*a* that rotatably connects the holder 110 to the plurality of power transmission units 210.

In an embodiment of the present invention, when the dual parallelogram module 200 that performs a motion driving of two degrees of freedom of pitch and roll driving by the plurality of power transmission units 210 and the linear drive module 300 that transmits a linear driving force to the dual parallelogram module 200 are driven, a slight vibration may occur throughout the entire surgical device 10, and coupling between the holder 110 of the surgical instrument module 100 and the dual parallelogram module 200 may become unstable. The slight vibration may significantly reduce precision and stability during surgery performed by using the surgical instrument module 100.

On the other hand, as with the above-described embodiment of the present invention, the pre-load part 130 disposed on the holder 110 and rotatably connected to the plurality of power transmission units 210 may press the coupling shaft 130*a* that rotatably connects the holder 110 to the plurality of power transmission units 210, the coupling between the holder 110 of the surgical instrument module 100 and the dual parallelogram module 200 may be stably maintained although the vibration occurs in the surgical device 10 due to the driving of the dual parallel program module 200 and the linear drive module 300. Accordingly, surgery may be performed more precisely and stably by the surgical instrument module 100.

Referring to FIGS. 13 and 14, the pre-load part 130 may include a reference bearing 132 and a pressure bearing 134.

The reference bearing 132 may rotatably support the coupling shaft 130*a*.

The pressure bearing 134 may press the reference bearing 132. Here, the pressure bearing 134 may be disposed at the outside of the reference bearing 132 to press an outer circumferential surface of the reference bearing 132.

Particularly, a pair of pressing bearings 134 may be disposed at both sides of the reference bearing 132, respectively.

That is, the pair of pressure bearings 134 may be disposed at the both sides of the reference bearing 132 in the left and right direction (Y-axis direction), respectively, to press the outer circumferential surface of the reference bearing 132 from the outside thereof.

As described above, the reference bearing 132 that rotatably supports the coupling shaft 130*a* may be pressed through the pressing bearings 134 disposed at the both sides of the reference bearing 132, the coupling between the holder 110 of the surgical instrument module 100 and the dual parallelogram module 200 may be more stably maintained although the vibration occurs in the surgical device 10 due to the driving of the dual parallel program module 200 and the linear drive module 300.

In an embodiment, the pressing bearing 134 may press the reference bearing 132 in an inclined manner.

That is, the pair of pressure bearings 134 may be disposed at the both sides of the reference bearing 132 in the left and right direction (Y-axis direction), respectively, to press the outer circumferential surface of the reference bearing 132 from the outside thereof in the inclined manner.

Particularly, a center in a radial direction of the pressing bearing 134 may be spaced apart from a center in a radial direction of the reference bearing 132 when viewed in the vertical direction. That is, when viewed in the vertical direction, as the center in the radial direction of the pressing bearing 134 is spaced apart from the center in the radial direction of the reference bearing 132, the pressing bearing 134 may press the outer circumferential surface of the reference bearing 132 from the outside in the inclined manner.

As described above, since the pair of pressing bearings 134 may obliquely press the reference bearing 132 at the both sides of the reference bearing 132, more greater pressing force may be applied to the reference bearing 132 in comparison with a case when the pressing bearings 134 press the reference bearing 132 on the same horizontal plane. Accordingly, the coupling between the holder 110 of the surgical instrument module 100 and the dual parallelogram module 200 may be more stably maintained although the vibration occurs in the surgical device 10 due to the driving of the dual parallel program module 200 and the linear drive module 300.

Referring to FIGS. 11 to 14 again, the holder 110 may include a first frame 112 and a second frame 114.

The first frame 112 may be rotatably connected to one of the plurality of power transmission units 210. For example, the first frame 112 may be connected to the first power transmission unit 210*a*.

The second frame 114 may be connected to another of the plurality of power transmission units 210 and disposed above the first frame 112. For example, the second frame 114 may be connected to the second power transmission unit 210*b*.

Also, the pre-load part 130 may be disposed on each of the first frame 112 and the second frame 114. That is, one of the pre-load parts 130 may be disposed on the first frame 112 and rotatably connected to the first power transmission unit 210*a*. Also, the other of the pre-load parts 130 may be disposed on the second frame 114 and rotatably connected to the second power transmission unit 210*b*.

According to the embodiment, since all of the pair of coupling shafts 130*a* connected to the two power transmission units (the first power transmission unit 210*a* and the second power transmission unit 210*b*) may be pressed obliquely, the coupling between the holder 110 of the surgical instrument module 100 and the dual parallel program module 200 may be more stably maintained.

On the other hand, as illustrated in FIGS. 13 and 14, in the pre-load part 130 disposed on the first frame 112, the pressing bearing 134 may press the reference bearing 132 obliquely in a downward direction.

Also, in the pre-load unit 130 disposed on the second frame 114, the pressing bearing 134 may press the reference bearing 132 obliquely in an upward direction.

According to the embodiment, since all of the pair of coupling shafts 130*a* connected to the two power transmission units (the first power transmission unit 210*a* and the second power transmission unit 210*b*) may be pressed, the coupling between the holder 110 of the surgical instrument module 100 and the dual parallel program module 200 may be more stably maintained.

Particularly, the pre-load part 130 may further include an auxiliary bearing 132*a*

The auxiliary bearing 132*a* may be disposed between an inner circumferential surface of the reference bearing 132 and an outer circumferential surface of the coupling shaft 130*a*. Although the auxiliary bearing 132*a* may be a ball bearing, the embodiment of the present invention is limited thereto.

Specifically, the auxiliary bearing 132*a* may surround the coupling shaft 130*a*.

Also, the coupling shaft 130*a* may be coupled to a center in the vertical direction and left and right direction (Y-axis direction) of the side surface connected to the dual parallelogram module 200 in the holder 110.

Here, when the press bearing 134 presses the outer circumferential surface of the reference bearing 132, a spaced space between the auxiliary bearing 132*a* surrounding the coupling shaft 130*a* in the reference bearing 132 and an inner circumferential surface of the reference bearing 132 may be minimized.

Particularly, since the coupling shaft 130*a* is coupled to the center in the vertical direction and left and right direction (Y-axis direction) of the side surface connected to the dual parallelogram module 200 in the holder 110, when the pressing bearing 134 presses the coupling shaft 130*a* so that the spaced space between the auxiliary bearing 132*a* and the inner circumferential surface of the reference bearing 132 is minimized, the coupling between the holder 110 of the surgical instrument module 100 and the dual parallelogram module 200 may be more stably maintained although a vibration occurs in the surgical device 10 due to the driving of the dual parallel program module 200 and the linear drive module 300.

Figure 15:
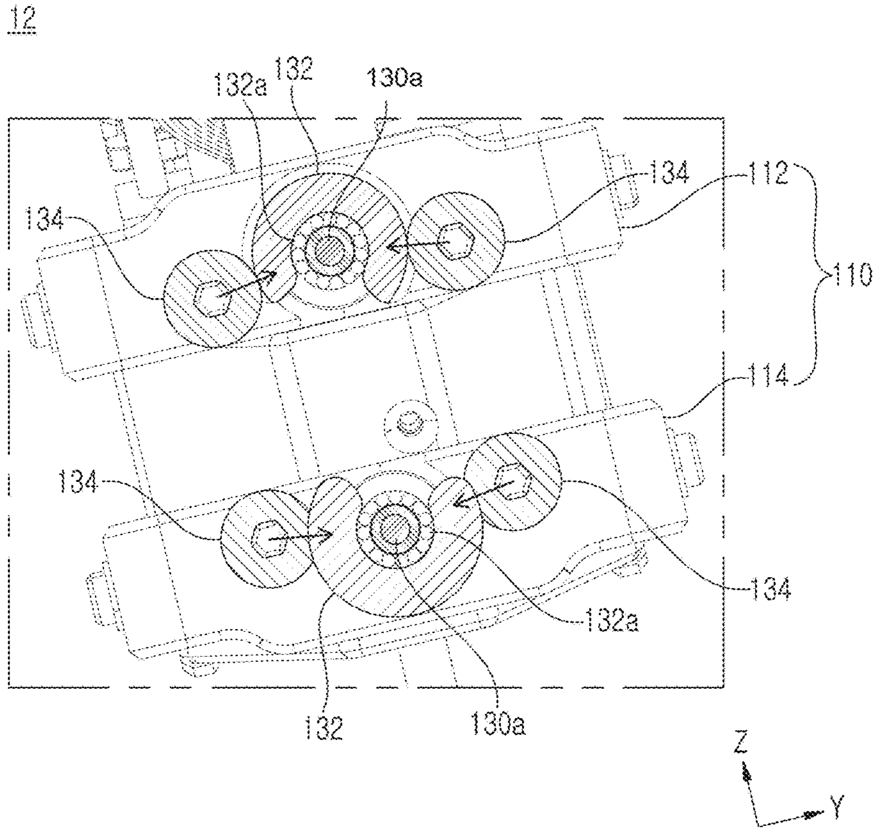
FIG. 15 is a view illustrating a surgical device according to an embodiment of the present invention.

FIG. 15 is a view illustrating a surgical device 12 according to another embodiment of the present invention.

Since the surgical device 12 according to this embodiment is similar to the surgical device 10 according to the previous embodiment, a redundant description of components that are substantially the same or similar to those of the previous embodiment will be omitted, and hereinafter, different aspects from the previous embodiment will be mainly described.

Referring to FIG. 15, in the surgical device 12, a pressing bearing 134 in a pre-load part 130 disposed on a first frame 112 may press a reference bearing 132 obliquely in an upward direction.

Also, in the pre-load unit 130 disposed on a second frame 114, the pressing bearing 134 may press the reference bearing 132 obliquely in a downward direction.

According to the embodiment, since all of a pair of coupling shafts 130*a* connected to two power transmission units (a first power transmission unit 210*a* and a second power transmission unit 210*b*) may be pressed, coupling between a holder 110 of a surgical instrument module 100 and a dual parallel program module 200 may be more stably maintained.

Figure 16:
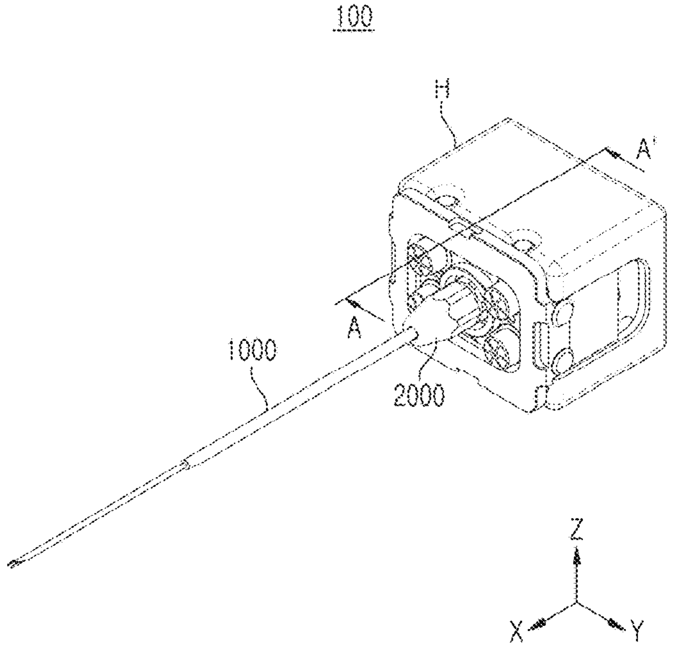
FIG. 16 is a view illustrating the surgical device according to the present invention.
Figure 17:
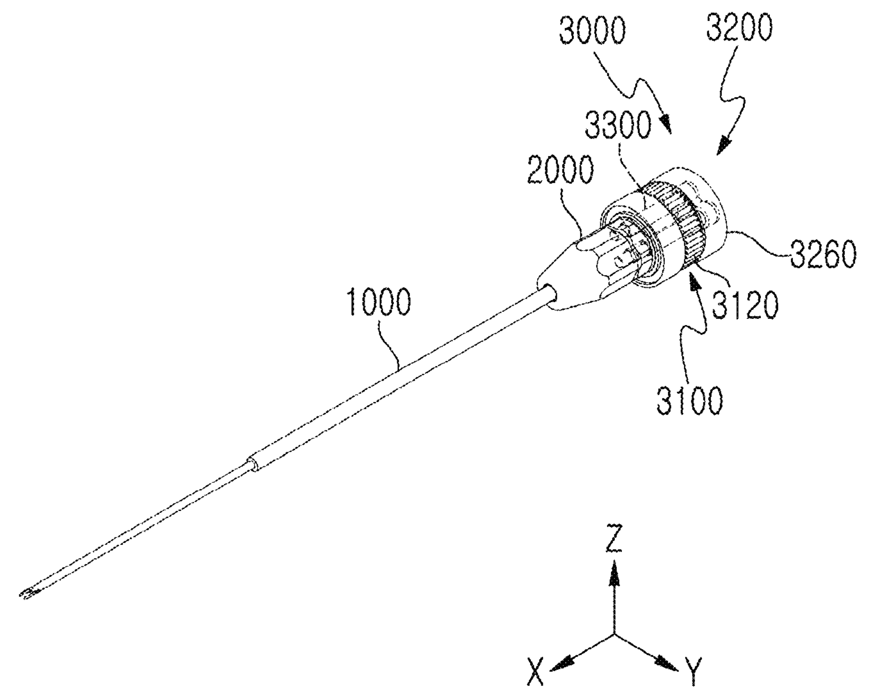
FIGS. 17 and 18 are views illustrating some components of the surgical device of FIG. 16.
Figure 18:
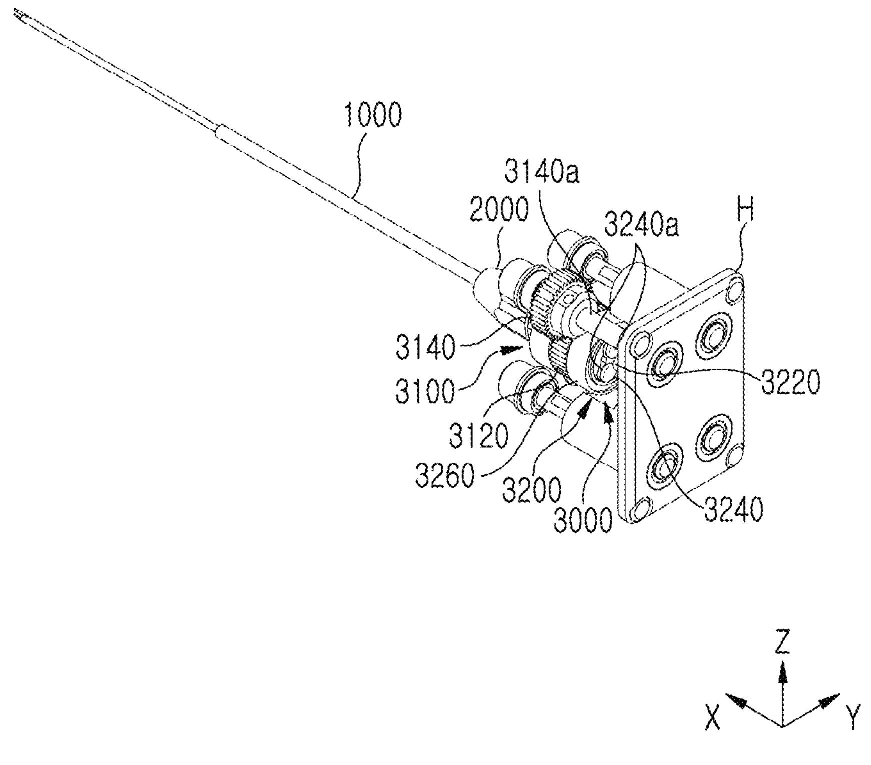
Figure 19:
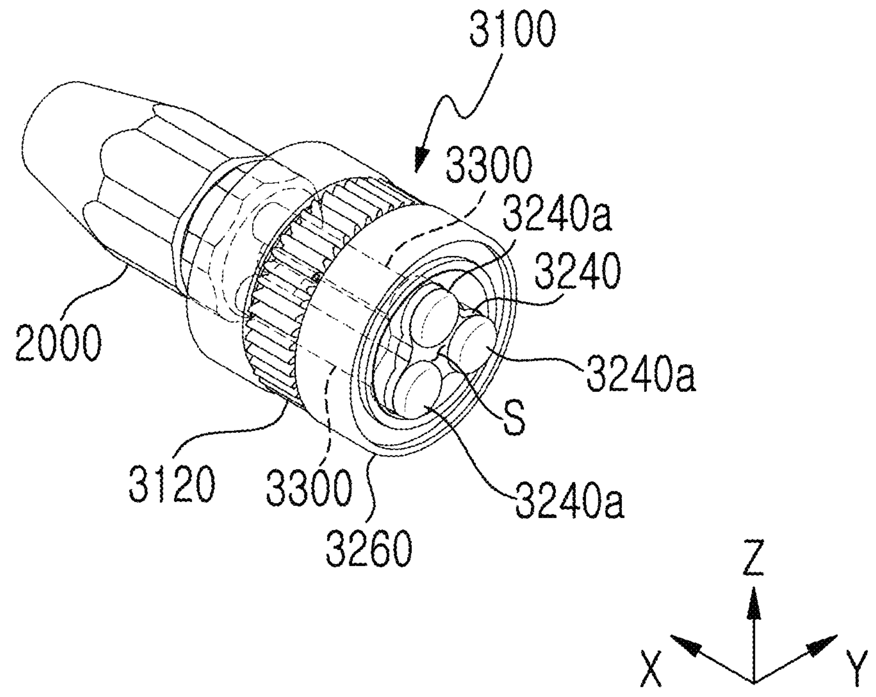
FIG. 19 is an enlarged view illustrating a portion of FIG. 18.
Figure 20:
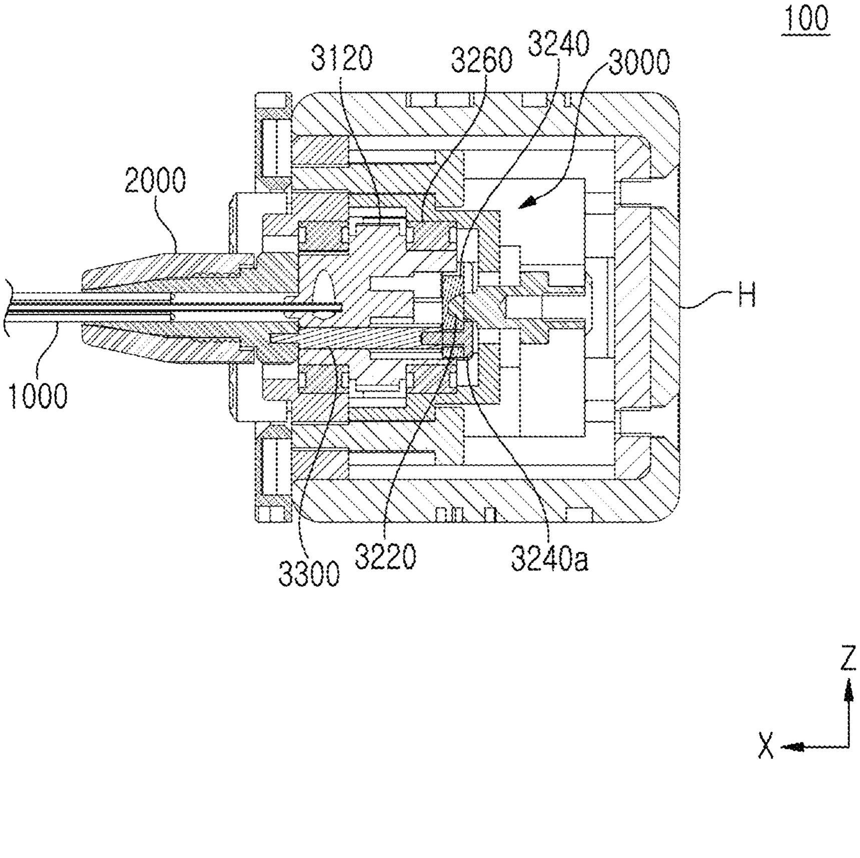
FIG. 20 is a cross-sectional view taken along line A-A' of FIG. 16.

FIG. 16 is a view illustrating the surgical device 100 according to an embodiment of the present invention, FIGS. 17 and 18 are views illustrating some components of the surgical device 100 of FIG. 16, FIG. 19 is an enlarged view illustrating a portion of FIG. 18, and FIG. 20 is a cross-sectional view taken along line A-A' of FIG. 16.

Referring to FIGS. 16 to 20, the surgical device 100 according to an embodiment of the present invention may include a surgical instrument 1000, a holder 2000, and a holder drive unit 3000. For example, the surgical device 100 may perform surgery on a human body.

The surgical instrument 1000 may include a gripper, which grips a portion (e.g., retina) of the human body, at an end thereof.

The holder 2000 may support the surgical instrument 1000.

The holder drive unit 3000 may simultaneously guide rotational driving and linear driving of the holder 2000. That is, the holder drive unit 3000 may simultaneously guide the rotational driving and the linear driving of the surgical instrument 1000 supported by the holder 2000. Accordingly, the surgical instrument 1000 may perform more various operations by simultaneously performing the rotational driving and the linear driving. A detailed configuration and operation of the holder drive unit 3000 will be described in more detail in a related description that will be described later.

According to the embodiment, the surgical instrument 1000 may perform more various operations than a typical surgical device that performs only the rotation or linear driving.

Referring to FIGS. 17 to 20, the holder drive unit 3000 may include a rotary drive unit 3100 and a linear drive unit 3200.

The rotary drive unit 3100 may guide rotational driving of the holder 2000. For example, the rotary drive unit 3100 may be driven by a separate servo motor (not shown).

The linear drive unit 3200 may guide linear driving of the holder 2000. For example, the rotary drive unit 3200 may be driven by a separate servo motor (not shown).

Also, the holder drive unit 3000 may further include a connector 3300.

The connector 3300 may connect the rotary drive unit 3100, the linear drive unit 3200, and the holder 2000 in the forward and backward direction (X-axis direction) of the surgical device 100. For example, the connector 3300 may extend lengthily along the forward and backward direction (X-axis direction) of the surgical device 100.

That is, as illustrated in FIGS. 17 to 20, the connector 3300 may connect the rotary drive unit 3100 that guides the rotational driving of the holder 2000 and the linear drive unit 3200 that guides the linear driving of the holder 2000 on the same line along the forward and backward direction (X-axis direction) of the surgical device 100. In other words, a central axis (X-axis) of a drive line in the forward and backward direction (X-axis direction) of the surgical device 100 of the linear drive unit 3200 and a drive axis (X-axis) of the rotary drive unit 3100 may be the same as each other.

According to the embodiment, since the holder drive unit 3000 may simultaneously guide the rotational driving and the linear driving of the holder 2000 supporting the surgical instrument 1000 on the same line, the surgical instrument 1000 may perform more various operations with more compact configurations.

Particularly, the connector 3300 may be provided in plurality. Also, the plurality of connectors 3300 may be spaced a predetermined distance from each other along a circumferential direction of the holder 2000. Accordingly, the connection between the rotary drive unit 3100, the linear drive unit 3200, and the holder 2000 in the forward and backward direction (X-axis direction) of the surgical device 100 may be more stably maintained.

Specifically, referring to FIGS. 17 to 19, the rotary drive unit 3100 may be disposed ahead of the linear drive unit 3200 when viewed from the forward and backward direction (X-axis direction) of the surgical device 100.

On the contrary, although not shown, the rotary drive unit 3100 may be disposed behind the linear drive unit 3200 when viewed from the forward and backward direction (X-axis direction) of the surgical device 100.

As described above, when viewed from the forward and backward direction (X-axis direction) of the surgical device 100, the rotary drive unit 3100 and the linear drive unit 3200 may be spaced apart from each other to minimize mutual interference between the rotational driving and the linear driving of the holder 2000.

Referring to FIGS. 18 and 20, the rotary drive unit 3100 may include a main gear 3120 and a drive gear 3140.

The main gear 3120 may guide the rotational driving of the holder 2000. Here, the main gear 3120 may have a rotational axis on the same axis (X-axis) as that of the holder 2000.

The drive gear 3140 may be coupled with the main gear 3120 to rotate the main gear 3120. Here, the above-described servo motor (not shown) may be connected to the drive gear 3140. Also, referring to FIG. 18, the drive gear 3140 may be disposed outside the main gear 3120 to contact the main gear 3120.

Figure 21:
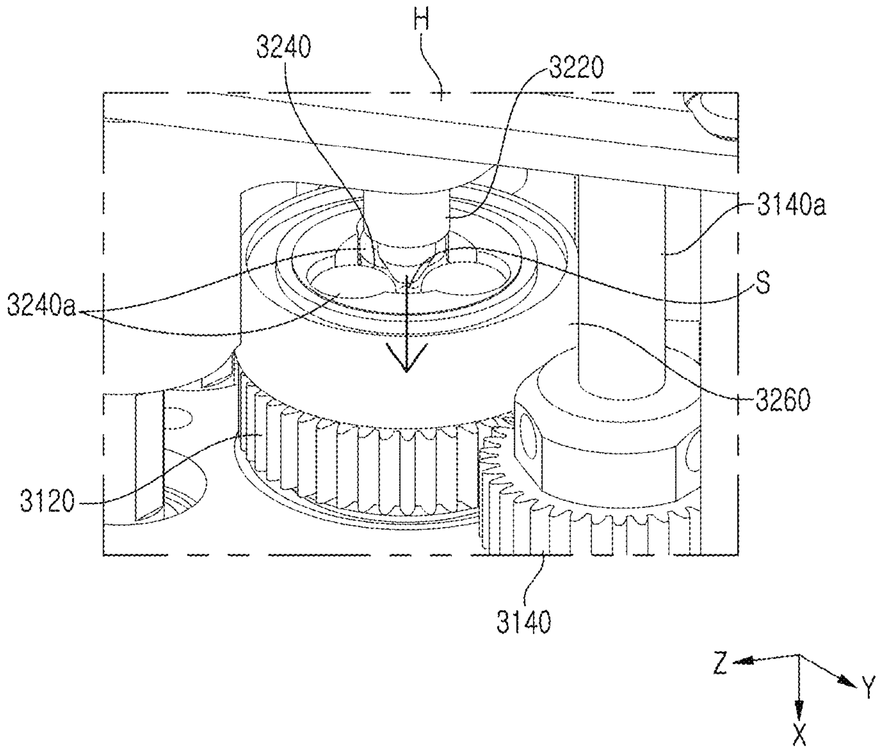
FIGS. 21 and 22 are views for explaining linear driving of the surgical device of FIG. 16.
Figure 22:
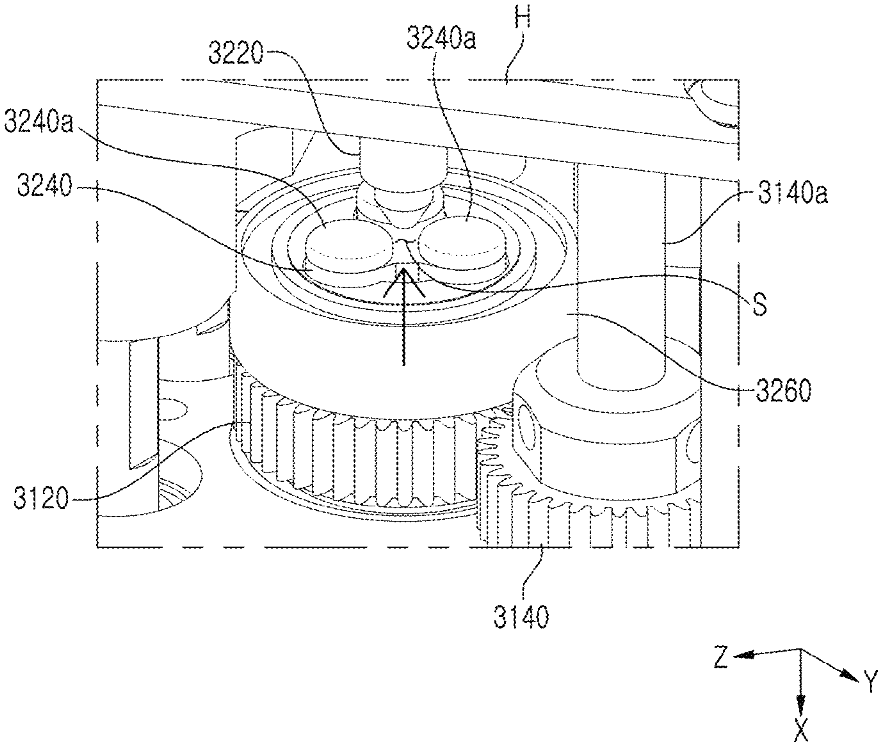

FIGS. 21 and 22 are views for explaining the linear driving of the surgical device 100 of FIG. 16. Here, FIG. 21 is a view illustrating a state in which a pressing part 3220 of the linear drive unit 3200 is moved forward, and FIG. 22 is a view illustrating a state in which the pressing part 3220 of the linear drive unit 3200 is moved backward.

Referring to FIGS. 18 to 22, the linear drive unit 3200 may include a pressing part 3220 and a pressure disk 3240.

The pressing part 3220 may be moved forward or backward so that the holder 2000 is driven in the forward and backward direction (X-axis direction) of the surgical device 100. In an embodiment, the pressing part 3220 may be connected to a portion of the holder 2000 and the inside of a housing H (refer to FIGS. 16 and 20) that accommodates the holder drive unit 3000 therein to protrude in the forward direction (X-axis direction) of the surgical device 100. Also, the pressing part 3220 may be driven by the separate servo motor (not shown).

The pressure disk 3240 may be connected through the holder 200 and the connector 3300. Also, the pressure disk 3240 may guide the holder 2000 to be moved forward or backward in the forward and backward direction of the surgical device 100 according to pressing or releasing of the pressing part 3220 in the forward and backward direction (X-axis direction) of the surgical device 100. In an embodiment, the pressure disk 3240 may have a plate shape having a predetermined area on a horizontal plane (YZ plane) and a predetermined thickness in the forward and backward direction (X-axis direction) of the surgical device 100.

Specifically, the pressure disk 3240 may be in surface-contact with a tip of the pressing part 3220 when the pressing part 3220 presses in the forward and backward direction (X-axis direction) of the surgical device 100. Also, when the pressure disk 3240 is moved forward in the forward direction of the surgical device 100 by the pressing part 3220, the pressure disk 3240 may move the connector 3300 forward in the forward direction of the surgical device 100. Accordingly, as the holder 2000 is moved forward in the forward direction of the surgical device 100, the surgical instrument 1000 may be also moved forward in the forward direction of the surgical device 100.

Also, when the pressing part is moved backward in the backward direction of the surgical device 100, the surface-contact between the pressure disk 3220 and the end of the pressing part 3220 may be released. In this case, the pressure disk 3240 may be moved backward in the backward direction of the surgical device 100. Also, the pressure disk 3240 may move the connector 3300 connected to the pressure disk 3240 backward in the backward direction of the surgical device 100. Accordingly, as the holder 2000 is moved backward in the backward direction of the surgical device 100, the surgical instrument 1000 may be also moved backward n the backward direction of the surgical device 100.

On the other hand, when viewed from the forward and backward direction of the surgical device 100, an elastic member (e.g., spring, not shown) may be disposed between the main gear 3120 and the pressure disk 3240 to elastically support the pressure disk 3240 in the backward direction of the surgical device 100. That is, when the pressing caused by the pressing part 3220 is released, the pressure disk 3240 may be moved in the backward direction of the surgical device 100 by an elastic force of the elastic member (not shown) and easily returned to an original position.

According to the embodiment, since the linear driving of the holder 2000 may be guided by the pressing and releasing between the pressure disk 3240 and the pressing part 3220, each of which has a predetermined area, the linear driving of the surgical instrument 1000 may be more stably guided.

Particularly, the connector 3300 may pass through the inside of the main gear 3120 in a radial direction and be connected to the pressure disk 3240.

For example, the main gear 3120 may have a hollow therein. Also, the connector 3300 connected to the holder 2000 may pass through the hollow of the main gear 3120 and be connected to the pressure disk 3240.

According to the embodiment, an interference between a rotational driving guide of the surgical instrument 1000 by the rotary drive unit 3100 and a linear driving guide of the surgical instrument 1000 by the linear drive unit 3200 may be minimized. Accordingly, the surgical instrument 1000 may perform more various operations at the same time.

Referring to FIGS. 20 to 22, the linear drive unit 3200 may further include a pressure disk accommodating part 3260.

The pressure disk accommodating part 3260 may accommodate the pressure disk 3240 therein and guide the driving of the pressure disk 3240 in the forward and backward direction (X-axis direction) of the surgical device 100 according to the driving of the pressing part 3220. Specifically, the pressure disk 3240 may be driven in the forward and backward direction of the surgical device 100 along an inner circumferential surface of the pressure disk accommodating part 3260. Accordingly, the pressure disk 3240 may be driven more stably in the forward and backward direction of the surgical device 100.

Referring to FIGS. 20 to 22, the pressure disk 3240 may include a protrusion 3240*a*.

The protrusion 3240*a* may be connected to the connector 3300 in the forward and backward direction (X-axis direction) of the surgical device 100 and contact the pressing part 3220 according to the driving of the pressing part 3220. For example, the protrusion 3240*a* may be a bolt.

In particular, the protrusion 3240*a* may protrude in a direction toward the pressing part 3220. That is, since the protrusion 3240*a* protrudes in the direction toward the pressing part 3220, when the pressing part 3220 is moved forward in the forward direction of the surgical device 100, the pressing part 3220 may be more easily moved forward in the forward direction of the surgical device 100 while pressing the protrusion 3240*a*.

Also, the protrusion 3240*a* may be provided in plurality. Also, the plurality of protrusions 3240*a* may be spaced a predetermined distance from each other along a circumferential direction of the pressure disk 3240.

Particularly, the plurality of protrusions 3240*a* may form an insertion space S into which the tip of the pressing part 3220 is inserted at a center in a radial direction of the pressure disk 3240.

Specifically, as illustrated in FIGS. 21 and 22, when the pressing part 3220 is moved forward in the forward direction of the surgical device 100, the plurality of protrusions 3240*a* surround the tip of the pressing part 3220 in the insertion space S on the horizontal plane (YZ plane). Accordingly, when the pressing part 3220 is moved forward toward the pressure disk 3240 to press the pressure disk 3240, the pressing part 3220 may stably press the pressure disk 3240 in the forward and backward direction of the surgical device 100 without being deviated from the pressure disk 3240 on the horizontal plane (YZ plane).

Here, as illustrated in FIGS. 21 and 22, the tip of the pressing part 3220 may be gradually inclined in the forward direction of the surgical device 100.

On the other hand, when the pressing part 3220 is moved forward in the forward and backward direction (X-axis direction) of the surgical device 100, outer circumferential surfaces of the plurality of protrusions 3240*a* may contact the tip of the pressing part 3220.

That is, when the pressing part 3220 is moved forward in the forward and backward direction (X-axis direction) of the surgical device 100, the outer circumferential surfaces of the plurality of protrusions 3240*a* may contact the tip of the pressing part 3220, which is gradually inclined in the forward direction of the surgical device 100.

When the tip of the pressing part 3220 is gradually inclined in the forward direction of the surgical device 100, friction and vibration generated by the surface-contact between the tip of the pressing part 3220 and the pressure disk 3240 may be minimized in comparison with a case when the tip of the pressing part 3220 has the same cross-sectional area as that in the forward and backward direction of the surgical device 100.

According to the embodiment, when the linear driving of the holder 2000 by the pressing part 3220 and the rotational driving of the holder 2000 by rotation of the main gear 3120 are simultaneously performed, the friction and vibration generated by the surface-contact between the tip of the pressing part 3220 and the pressure disk 3240 may be minimized, and various operation of the surgical device 1000 may be stably performed at the same time.

Figure 23:
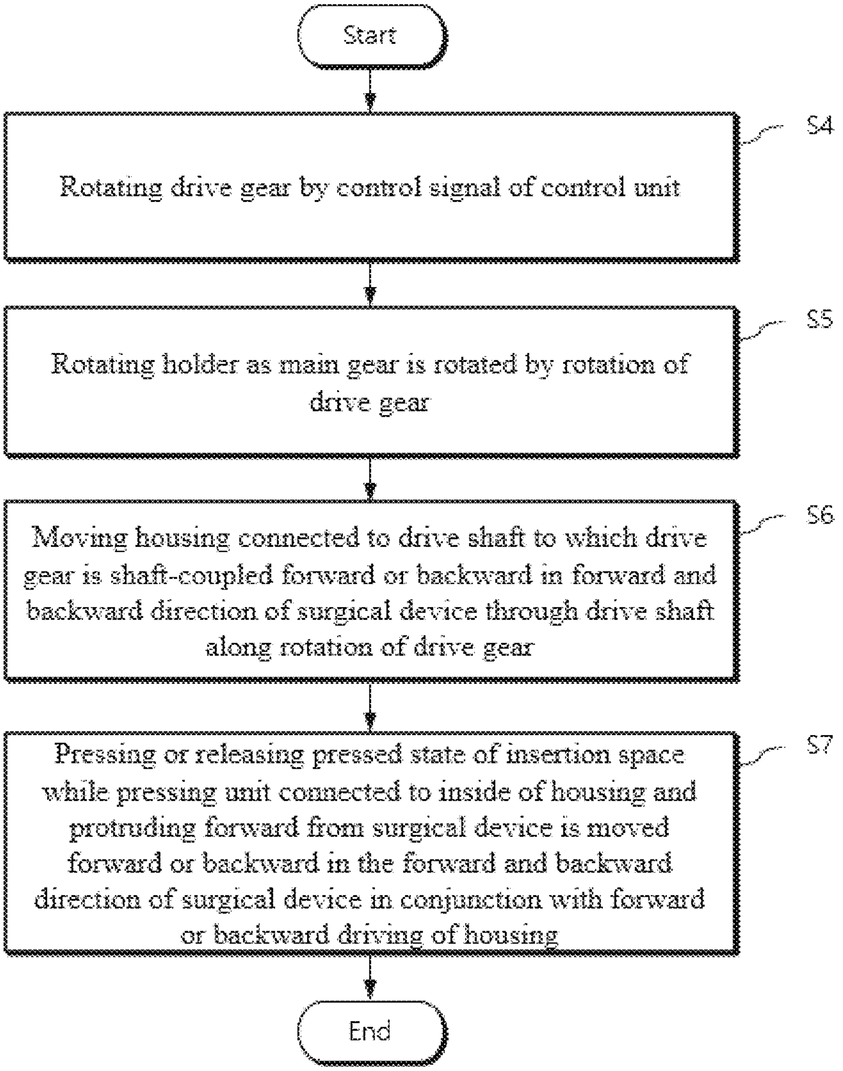
FIG. 23 is a flowchart representing a method of operating a surgical device by using the surgical device of FIG. 16.
Figure 24:
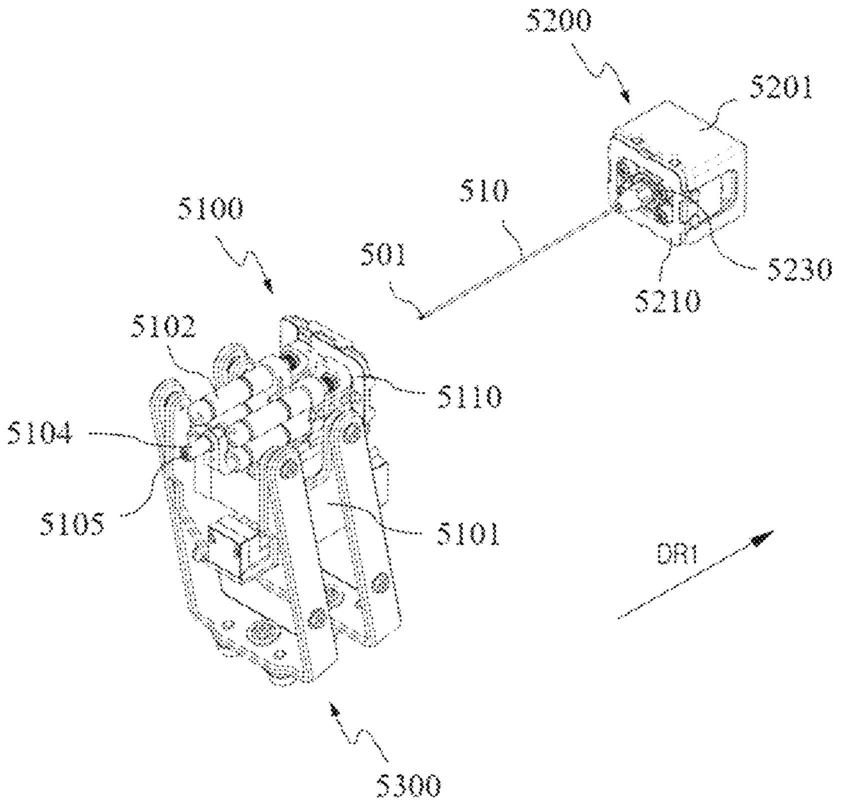
FIG. 24 is an exploded perspective view illustrating the surgical device including an arm module according to the present invention.
Figure 25:
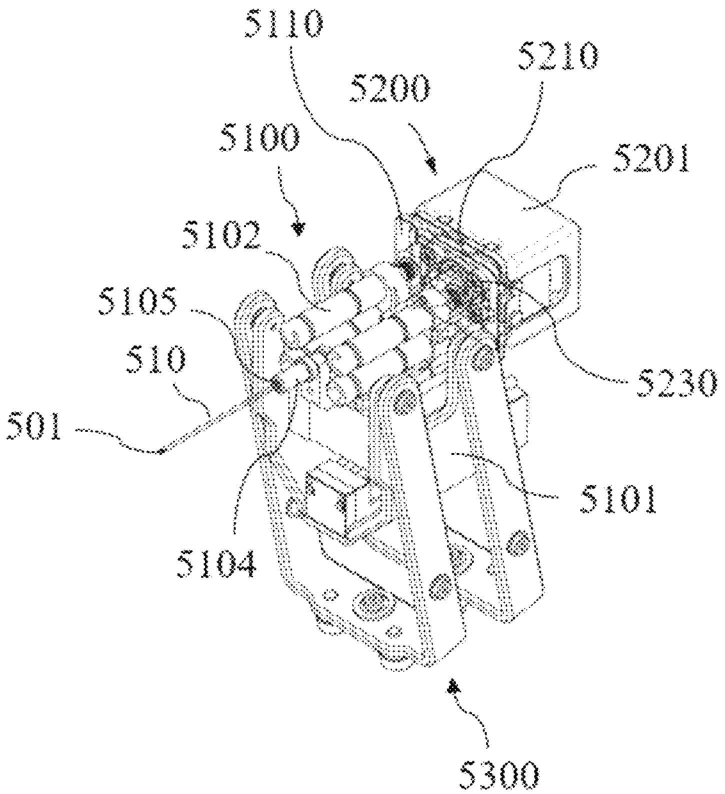
FIG. 25 is an assembled perspective view illustrating the surgical device including the arm module according to the present invention.
Figure 26:
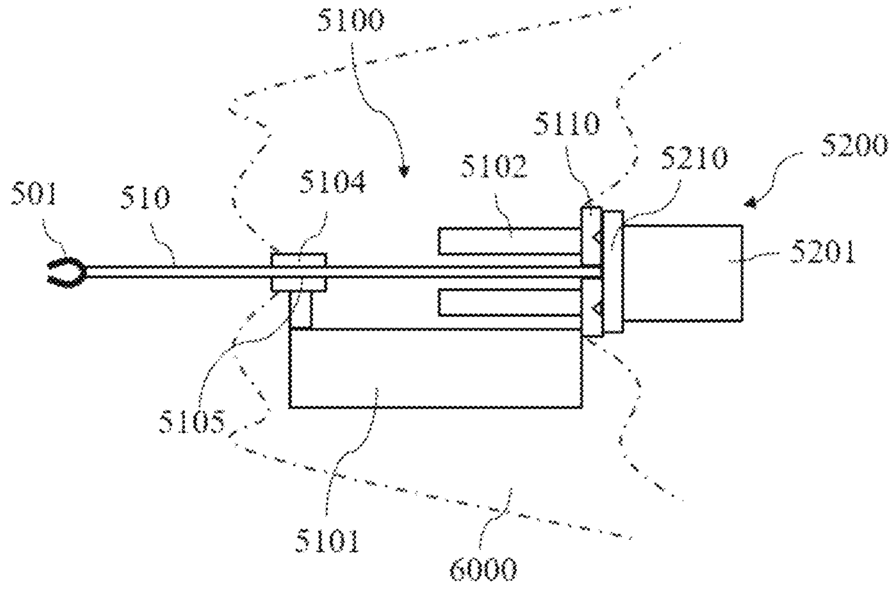
FIG. 26 is a schematic side view of FIG. 25.
Figure 27:
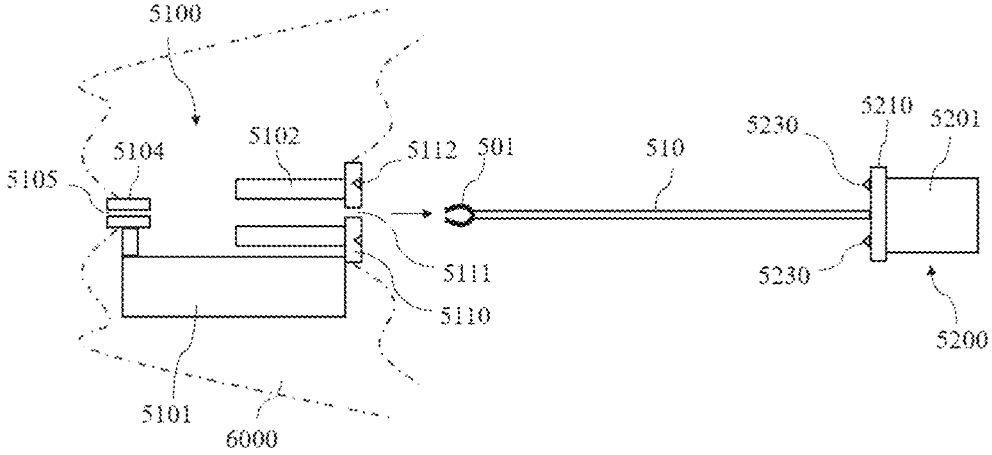
FIG. 27 is a schematic side view of FIG. 24.

FIG. 23 is a flowchart representing a method of operating a surgical device by using the surgical device 10 of FIG. 16.

Referring to FIG. 23 together with FIGS. 16 to 22, the method of operating the surgical device according to an embodiment of the present invention may include steps S4 to S7 as stated below.

In the step S4, the drive gear may be rotated by a control signal of a control unit (not shown). Here, the above-described holder drive unit 3000 may include the control unit. For example, the control unit may include a processor. Here, the processor may be realized into CPU, GPU, AP, each of which has a calculation function or a combination thereof, and provided together with various types of memories such as DRAM, a flash memory, and SSD as necessary. The control unit may control simultaneous rotational and linear driving of the holder 2000 that supports the surgical instrument 1000 according to the command input by the user.

Specifically, the rotary drive unit 3100 may further include a driving shaft 3140*a* and the servo motor (not shown). Here, the drive gear 3140 may be shaft-coupled to the driving shaft 3140*a*, and the driving shaft 3140*a* may be connected to the servo motor and rotated according to the driving of the servo motor. Also, the control unit may control the servo motor. In an embodiment, the driving shaft 3140*a* may be a lead screw. However, the embodiment of the present invention is not limited thereto.

In the step S5, as the main gear 3120 is rotated by rotation of the drive gear 3140, the holder 2000 is rotated. Thus, the surgical instrument 1000 connected to the holder 2000 may be also rotated.

In the step S6, the housing H connected to the driving shaft 3140*a* that is shaft-coupled to the drive gear 3140 is moved forward or backward in the forward and backward direction of the surgical device 100 through the driving shaft 3140*a* according to the rotation of the drive gear 3140. Here, the housing H may be screw-coupled with the driving shaft 3140*a* so as to be easily moved forward or backward in the forward and backward direction of the surgical device 100 through the driving shaft 3140*a* when the drive gear 3140 is rotated.

In the step S7, the pressing part 3220 connected to the inside of the housing H and protruding in the forward direction of the surgical device 100 is moved forward or backward in conjunction with the forward or backward driving of the housing H to press or release the insertion space S. Accordingly, the surgical instrument 1000 connected to the holder 2000 may be moved forward or backward in the forward and backward direction of the surgical device 100.

As described above, since the rotational driving and linear driving of the surgical instrument 1000 may be performed simultaneously through the rotation of the drive gear 3140 according to the control signal of the control unit, various surgical operations by the surgical instrument 1000 may be stably implemented at the same time.

A surgical device 5300 may include an arm module 5100 and a surgical instrument module 5200.

The arm module 5100 may include at least one of a base 5101, a guide tube 5104, a motor 5102, a first interface 5110, and a first coupler 5112.

The surgical instrument module 5200 may include at least one of a housing 5201, a second interface 5210, a second coupler 5230, an elongated body 510, and an end effector 501.

The arm module 5100 may maintain a position and an angle of the guide tube 5104 at a predetermined position with respect to an eye that is a subject of precision surgery. The arm module 5100 may include a plurality of operating arms having a parallelogram structure. The operating arms having the parallelogram structure may be more robust than a robot arm having a cantilever structure in terms of a position error, an angular error, a translational movement error, a rotational movement error, vibration, a backlash, hysteresis, and a nonlinear error. The plurality of operating arms may form a moving unit for the precise surgery.

While the robot arm having the cantilever structure is used for general surgery requiring moderate precision, the arm module 5100 according to the present invention may be used for surgery requiring high precision such as eye surgery of the present invention. When the arm module 5100 according to the present invention has, e.g., a rotational degree of freedom around x-axis, the plurality of arms having the parallelogram structure move to realize the corresponding degree of freedom. Thus, the plurality of arms may be more robust to various errors and improve surgical precision than the single arm such as a cantilever.

The guide tube 5104 may support the elongated body 510 of the surgical instrument module 5200 at a position adjacent to the eye that is the subject of the surgery. The elongated body 510 that is vulnerable to vibration or bending during high precision surgery may have both ends supported by the guide tube 5104 and the housing 5201. The elongated body 510 may have a support structure having a both ends supported beam shape in which both ends are supported by the guide tube 5104 of the arm module 5100 and the surgical instrument module 5200.

When the arm module 5100 is capable of performing rotational movement with two degrees of freedom and transitional movement with two degrees of freedom, the arm module 5100 may set the position and angle of the guide tube 5104 to a desired position and angle while performing the rotational movement with two degrees of freedom and the transitional movement with two degrees of freedom.

Various kinds of surgical instrument modules 5200 may be attached to and detached from the arm module 5100 for replacement depending on a surgical procedure. As a result, the elongated body 510 of the surgical instrument module 5200 may be attached to and detached from the guide tube 5104 that is set to the desired position and angle by the arm module 5100.

A coupling surface between the surgical instrument module 5200 and the arm module 5100 may be obtained by a method in which the first interface 5110 of the arm module 5100 and the second interface 5210 of the surgical instrument module 5200 are coupled while facing each other. The coupling surface between the surgical instrument module 5200 and the arm module 5100 may include the first interface 5110 of the arm module 5100 and the second interface 5210 of the surgical instrument module 5200, which are coupled to each other.

The coupling surface between the surgical instrument module 5200 and the arm module 5100 or between the first interface 5110 and the second interface 5210 may correspond to a sterilization interface. Based on the sterilization interface, a portion on which the arm module 5100 is disposed may correspond to a sterilized portion and be wrapped by sterilization vinyl 6000 for repeated use. Based on the sterilization interface, a portion on which the surgical instrument module 5200 is disposed may correspond to a non-sterilized portion and be discarded after being used a certain number of times.

The surgical instrument module 5200 may be discarded after being used a certain number of times because the surgical instrument module is only sterilized to a predetermined level and exposed to the same space as the subject of the surgery.

Thus, it is recommended that only the minimum number of components are mounted to the surgical instrument module 5200 that is a disposable portion. The surgical instrument module 5200 may include the housing 5201, the wire, a pulley around which the wire is wound, and the second coupler 5230 connected to the pulley. Expensive components such as the motor 5102 and a motor control unit may be installed on the arm module 5100 that is the sterilized portion.

The motors 5102 may be arranged annularly or with equal intervals around a first hole 5111 or a guide tube hole 5105 for vibration reduction or mass distribution.

The pulley around which the wire is wound is also preferably installed on the arm module 5100. In this case, however, since the coupling surface between the first interface 5110 and the second interface 5210 inevitably has a structure in which the wire is coupled and separated, this structure may not be substantially realized. Thus, inevitably, the first interface 5110 and the second interface 5210 have a structure in which the first coupler 5112 and the second coupler 5230 are attached to and detached from each other, and the discarded surgical instrument module 5200 has a structure in which the pulley and the wire, as the minimum number of components, are installed in the housing 5201.

When the surgical instrument module 5200 is mounted to the arm module 5100, the surgical instrument module 5200 may move from a distal direction that is a direction away from the subject of the surgery to a proximal direction that is a direction adjacent to the subject of the surgery.

When the second interface 5210 of the surgical instrument module 5200 is coupled to the first interface 5110 of the arm module 5100, the surgical instrument module 5200 may be completely mounted. When the surgical instrument module 5200 is coupled, the elongated body and the end effector 501 may sequentially pass through the first hole 5111 of the first interface 5110 and the guide tube hole 5105 of the guide tube 5104. The motor 5102 of the arm module 5100 may be disposed between the first hole 5111 and the guide tube hole 5105. The first hole 5111, the guide tube hole 5105, and the arm module 5100 may correspond to the sterilized portion that is used repeatedly instead of being discarded and be wrapped by sterilization vinyl 6000. An opened portion of the sterilization vinyl 6000 may be the first hole 5111 and the guide tube hole 5105, to which the elongated body is mounted. A portion except for the first hole 5111 and the guide tube hole 5105 may be sealed by the sterilization vinyl 6000.

When the surgical instrument module 5200 is separated from the arm module 5100, the second interface 5210 of the surgical instrument module 5200 may be separated from the first interface 5110 of the arm module 5100. The surgical instrument module 5200 may be completely separated when the surgical instrument module 5200 moves from the proximal direction to the distal direction. When the surgical instrument module 5200 is separated, the elongated body and the end effector 501 may sequentially pass through the guide tube hole 5105 and the first hole 5111 of the first interface 5110. The motor 5102 of the arm module 5100 may be disposed between the first hole 5111 and the guide tube hole 5105. Various kinds of surgical instrument modules 5200 may be coupled or separated during the surgical procedure. The surgical instrument module 5200 that is repeatedly used may be discarded and replaced with the new surgical instrument module 5200 to prevent infection of a patient. To this end, the first hole 5111 and the guide tube hole 5105 may be defined.

The arm module 5100 may have a structure in which the guide tube hole 5105, the motor 5102, and the first hole 5111 of the first interface 5110 are sequentially arranged in a direction from a proximal portion to a distal portion.

The surgical instrument module 5200 may have a structure in which the end effector 501, the elongated module, the second interface 5210, and the housing 5201 are sequentially arranged in the direction from the proximal portion to the distal portion.

The first interface 5110 may include the first coupler 5112 connected to the motor 5102. The second interface 5210 may include the second coupler 5230 connected to the wire or pulley in the housing 5201. A torque of the motor 5102 may be transmitted to the pulley in the housing 5201 by the first coupler 5112 and the second coupler 5230 that are coupled in an axial direction. Rotation of the pulley may be converted into tension of the wire. The wire extending into the elongated body 510 may use the tension to operate the end effector 501.

Since the first interface 5110 and the second interface 5210 form the coupling surface, the housing 5201 of the surgical instrument module 5200 may be exposed to the non-sterilized portion or the same space as the subject of the surgery.

According to the embodiment of the present invention, since the motion driving with two degrees of freedom of the surgical instrument module through the dual parallelogram module may be realized by transmitting the linear driving force to the dual parallelogram module, the surgical instrument module may be more precisely driven than the method of driving the dual parallelogram module simply through the rotational driving force. Thus, more precise surgery may be performed by the surgical instrument module, and the safety accident occurring during the surgery may be prevented through the precise driving of the surgical instrument module.

Also, according to the embodiment of the present invention, since the linear driving force of the linear drive unit may be transmitted to the dual parallelogram module through the link that is rotatable with respect to both of the linear drive unit and the power transmission unit, the motion driving force of the two degrees of freedom according to the driving of the dual parallelogram module may be easily transmitted to the surgical instrument module. Thus, more precise surgery may be performed by the surgical instrument module.

Also, according to the embodiment of the present invention, since the linear drive unit that generates the linear driving force and the link rotatably connected to each of the linear drive unit and the power transmission unit may be provided in pair on the left and right, pitch and roll driving by the dual parallelogram module may be performed more stably.

Also, according to the embodiment of the present invention, since the first pivot joint that rotatably supports the link with respect to the moving block may be rotatably connected to the moving block that is linearly driven along the guide rail, when the linear driving force of the linear drive unit is transmitted to the link and converted into the rotational driving force, more various types of motion driving may be performed by the link. Accordingly, the pitch and roll driving performed by the dual parallelogram module may be more stably performed.

Also, since the pre-load part disposed on the holder and rotatably connected to the plurality of power transmission units may press the coupling shaft that rotatably connects the holder to the plurality of power transmission units, the coupling between the holder of the surgical instrument module and the dual parallelogram module may be stably maintained although the vibration occurs in the surgical device by the driving of the dual parallelogram module and the linear drive module. Accordingly, the surgery may be performed more precisely and stably by the surgical instrument module.

According to the embodiment of the present invention, the surgical instrument may perform more various operations than the typical surgical device that performs only the rotation or linear driving.

Specifically, according to the embodiment of the present invention, since the holder drive unit may simultaneously guide the rotational driving and the linear driving of the holder supporting the surgical instrument on the same line, the surgical instrument may perform more various operations with the more compact configuration.

Also, according to the embodiment of the present invention, since the linear driving of the holder may be guided by the pressing and releasing between the pressure disk having a predetermined area and the pressing part, the linear driving of the surgical instrument may be guided more stably.

Also, according to the embodiment of the present invention, the interference between the rotational motion guide of the surgical instrument by the rotary drive unit and the linear driving guide of the surgical instrument by the linear drive unit may be minimized. Accordingly, the surgical instrument may simultaneously perform more various operations.

In addition, according to the embodiment of the present invention, various other additional effects may be achieved. The above-described various effects of the present invention will be described in detail in each embodiment, or effects that are easily understandable by those skilled in the art will be omitted.

While the present invention has been particularly shown and described with reference to exemplary embodiments thereof, it will be understood by those of ordinary skill in the art that various changes in form and details may be made therein without departing from the spirit and scope of the present invention as defined by the following claims.

It will be apparent to those having skill in the art that orientations of constituent elements such as up, down, left, right, front, and back in the drawings are used for convenience in description and clarity and vary depending on the location of the target object or the observer.

DESCRIPTION OF THE REFERENCE NUMERALS

10: Surgical device
100: Surgical instrument module
110: Holder
111: Rotation bearing
112: First frame
114: Second frame
120: Surgical instrument
130: Pre-load part
130*a*: Coupling shaft
132: Reference bearing
132*a*: Auxiliary bearing
134: Pressure bearing
200: Dual parallelogram module
300: Linear drive module
310: Module body
320: Linear drive unit
322: Guide rail
324: Moving block
330: Link
340: First pivot joint
350: Second pivot joint
100: Surgical device
1000: Surgical instrument
2000: Holder
3000: Holder drive unit
3100: Rotary drive unit
3120: Main gear
3140: Drive gear
3200: Linear drive unit
3220: Pressing part
3240: Pressure disk
3240*a*: Protrusion
3260: Pressure disk accommodating part
3300: Connector
5100: Arm module
5101: Base
5102: Motor

5104: Guide tube
5105: Guide tube hole
5110: First interface
5111: First hole
5112: First coupler
5200: Surgical instrument module
501: End effector
510: Elongated body
5201: Housing
5210: Second interface
5230: Second coupler
5300: Surgical device
6000: Sterilization vinyl

What is claimed is:

1. A surgical device, comprising:

a surgical instrument module having a first side and a second side opposite the first side;

a dual parallelogram module coupled to the second side of the surgical instrument module, the dual parallelogram module having at least one power transmission unit configured to provide movement;

a linear drive module coupled to the at least one power transmission unit;

a holder disposed between the at least one power transmission unit and a surgical instrument; and a pre-load part disposed on the holder and rotatably connected to the at least one power transmission unit, wherein the linear drive module transmits a driving force to the dual parallelogram module, the dual parallelogram module has at least two degrees of freedom, the surgical instrument is operably coupled to the holder, and the pre-load part is configured to press a coupling shaft that rotatably connects the holder to the at least one power transmission unit.

2. The surgical device of claim 1, wherein the at least one power transmission unit comprises a plurality of power transmission units.

3. The surgical device of claim 1, wherein the dual parallelogram module further comprises a plurality of base links, and wherein, each base link is coupled to one of the plurality of power transmission units.

4. The surgical device of claim 1, wherein the dual parallelogram module further comprises a plurality of base links, and the at least one power transmission unit comprise:

a plurality of pitch links, wherein each of the plurality of pitch links is coupled to one of the plurality of base links in a vertical direction;

a roll link rotatably coupled to each of the plurality of base links;

a pitch joint rotatably coupled to each of the plurality of base links and the plurality of links thereby enabling pitch rotation; and a plurality of roll joints, wherein each of the plurality of roll joints is rotatably coupled to each of the plurality of base links thereby enabling roll rotation.

5. The surgical device of claim 1, wherein the dual parallelogram module is spaced a predetermined distance in a forward and backward direction of the surgical device, and the dual parallelogram module is coupled to the plurality of power transmission units and configured to couple the plurality of power transmission units in the vertical direction.

6. The surgical device of claim 1, further comprising a first pivot joint disposed on the moving block and having a lower side rotatably coupled to the moving block, wherein the first end of the drive link is rotatably connected to a side surface.

7. The surgical device of claim 1, wherein a power transmission unit of the at least plurality of transmission units disposed at a lowermost side of the plurality of power transmission units is configured to be connected to the base plate.

8. The surgical device of claim 1, wherein the linear drive module further comprises:

a base plate having a first end and a second end opposite the first end;

a plurality of guide rails disposed on the base plate;

a moving block slidably disposed on each of the plurality of guide rails;

a drive link rotatably coupled to the moving block at a first end; and a plurality of linear drive units operably coupled to the plurality of guide rails.

9. The surgical device of claim 8, further comprising a second pivot joint disposed on one of the plurality of transmission units, and wherein the second pivot joint is configured to surround a portion of the second end of the drive link such that the second drive link is rotatably coupled to the second pivot joint.

10. The surgical device of claim 8, wherein the plurality of guide rails comprises a first guide rail and a second guide rail, the plurality of linear drive units comprises a first drive unit and a second drive unit, and the first drive unit is operably coupled to the first guide rail and the second drive unit is operably coupled to the second guide rail.

11. The surgical device of claim 10, wherein, when each of the first and second drive units are linearly driven in a forward direction with respect to a longitudinal axis of the surgical device toward the first end of the base plate, the surgical instrument module is configured to be pitch-driven forwardly.

12. The surgical device of claim 10, wherein when each of the first and second drive units are linearly driven in a backward direction with respect to a longitudinal axis of the surgical device toward the second end of the base unit, the surgical instrument module is configured to be pitch-driven backward.

13. The surgical device of claim 10, wherein, when one of the first drive unit and the second drive unit is linearly driven toward the first end of the base plate and the other of the first and second drive units is linearly driven toward the second end of the base plate, the surgical instrument module is roll driven in left or right direction in with respect to a longitudinal axis of the surgical device.

14. The surgical device of claim 10, wherein, when the surgical instrument module is roll driven in left and right direction, a rotation angle of the surgical instrument module corresponds to a difference between a displacement of the any one of the first or second drive units to the first end of the base plate and the displacement of the of the other one of the first or second drive units to the second end of the base plate.

15. A surgical device system, comprising:

a surgical instrument comprising a surgical instrument module having a surgical tool for performing surgical operations, wherein the surgical instrument module comprises a first side and a second side opposite the first side, and the surgical instrument further includes a dual parallelogram module coupled to the second side of the surgical instrument module, the dual parallelogram module having at least one power transmission unit for providing movement; and a linear driving module coupled to the at least one of the power transmission unit, a holder disposed between the at least one power transmission unit and the surgical instrument; and a pre-load part disposed on the holder and rotatably connected to the at least one power transmission unit;

a power source module operably coupled to the surgical instrument for providing power to the surgical instrument; and a communication module integrated within the surgical instrument, the communication module configured to establish wireless communication between the surgical instrument and an external controller; wherein the linear driving module transmits a driving force to the dual parallelogram module, the dual parallelogram module has at least two degrees of freedom the surgical instrument is operably coupled to the holder, the pre-load part is configured to press a coupling shaft that rotatably connects the holder to the at least one power transmission unit, and the external controller comprises a user interface application, wherein the user interface application is configured to receive and process data transmitted from the surgical instrument device system via the communication module, and present visual feedback and control options to a user.

16. A method of operating a surgical device, the method comprising:

providing a surgical instrument module having a surgical instrument coupled to a first end and a dual parallelogram module coupled to a second end, the dual parallelogram module comprising at least one power transmission unit;

providing a linear driving module coupled to the at least one power transmission unit;

providing a holder disposed between the at least one power transmission unit and the surgical instrument, and a pre-load part disposed on the holder and rotatably connected to the at least one power transmission unit, actuating the linear driving module to transmit a driving force to the dual parallelogram module such that the surgical instrument performs at least one of a first driving motion, a second driving motion, or a third driving motion, and pressing a coupling shaft that rotatably connects the holder to the at least one power transmission unit.

* * * * *